United States Patent [19]

Schinazi et al.

[11] Patent Number: 5,118,672

[45] Date of Patent: Jun. 2, 1992

[54] 5'-DIPHOSPHOHEXOSE NUCLEOSIDE PHARMACEUTICAL COMPOSITIONS

[75] Inventors: Raymond F. Schinazi, Decatur, Ga.; Jean-Pierre Sommadossi, Vestavia, Ala.; Chung K. Chu, Athens; William M. Shafer, Stone Mountain, both of Ga.

[73] Assignees: University of Georgia Research Foundation, Athens; Emory University, Atlanta, both of Ga.; UAB Research Foundation, Birmingham, Ala.

[21] Appl. No.: 551,548

[22] Filed: Jul. 11, 1990

Related U.S. Application Data

[63] Continuation-in-part of Ser. No. 377,617, Jul. 10, 1989, which is a continuation-in-part of Ser. No. 104,438, Oct. 2, 1987, Pat. No. 4,916,122, which is a continuation-in-part of Ser. No. 7,473, Jan. 28, 1987, abandoned.

[51] Int. Cl.⁵ .................. A61K 31/70; A61K 31/385; A61K 31/38; A61K 43/08
[52] U.S. Cl. ........................ 514/47; 514/48; 514/51; 514/43.8; 514/441; 514/445; 514/461; 514/463; 514/473
[58] Field of Search ............ 874/747, 48, 51; 544/262, 264, 271, 276; 536/4.1, 122; 549/5-7, 30, 429, 430; 514/441, 438, 445, 461, 463, 473

[56] References Cited

U.S. PATENT DOCUMENTS

| | | | |
|---|---|---|---|
| 3,328,389 | 6/1967 | Shimizu et al. | 514/49 |
| 4,230,698 | 10/1980 | Bobek et al. | 514/49 |
| 4,847,244 | 7/1989 | Rideout et al. | 514/50 |
| 4,879,277 | 11/1989 | Mitsuya et al. | 514/49 |
| 4,916,122 | 4/1990 | Chu et al. | 514/49 |

FOREIGN PATENT DOCUMENTS

| | | |
|---|---|---|
| 0306597 | 3/1989 | European Pat. Off. |
| 0352248 | 2/1990 | European Pat. Off. |
| 0357571 | 3/1990 | European Pat. Off. |
| 2042290 | 2/1971 | France |
| 2051064 | 4/1971 | France |

OTHER PUBLICATIONS

Alarcon, et al., *Antimicrobial Agents and Chemotherapy* vol. 32, No. 8, Aug. 1988, pp. 1257-1261.
Roseman, et al., *Journal of the American Chemical Society*, vol. 83, Feb. 1961, pp. 659-663.
McDowell, et al., *Chemical Abstracts*, vol. 104, No. 1, Jan. 1986, p. 23.

(List continued on next page.)

*Primary Examiner*—John W. Rollins
*Attorney, Agent, or Firm*—Kilpatrick & Cody

[57] ABSTRACT

This invention provides compounds and pharmaceutical compositions that include compounds of the formula:

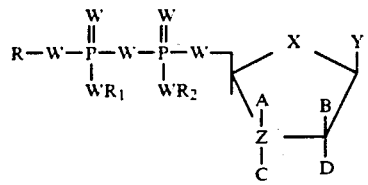

in which A, B, and C are hydrogen, halogen, or azido; D is hydrogen, halogen, azido, or OH; A and B or C and D can be replaced with a double bond; R is an aldohexose, aldohexosamine, or N-acetyl aldohexosamine, W is O or S; X is O, S, or $CH_2$; Y is a purine or pyrimidine base, Z is C, S, or O, and wherein when Z is S or O, A and C are not present. The compounds of this inverntion have enhanced pharmaceutical or biological activity or increased intracellular absorption compared to the corresponding parent nucleoside as a function of the 5'-diphosphohexose moiety. Many of these compounds have antiviral, including anti-HIV, activity. Others have antibacterial activity. In one embodiment, the invention is a method to treat HIV infection and opportunistic infections concomitantly.

9 Claims, 11 Drawing Sheets

OTHER PUBLICATIONS

Pazur, John D., *Chemical Abstracts*, vol. 90, No. 24, Jun. 11, 1979, p. 315.

Keppler, et al., *Metabolic Compartmentation*, 1982, pp. 147-203.

Datema, et al., *Pharmac. Ther.*, vol. 33, 1987, pp. 221-286.

Alcina, et al., *Antimicrobial Agents and Chemotherapy*, vol. 32, No. 9, Sep. 1988, pp. 1412-1415.

Eriksson, et al., *Antimicrobial Agents and Chemotherapy*, vol. 33, No. 10, Oct. 1989, pp. 1729-1734.

Chu, et al., *J. Med. Chem.*, vol. 32, 1989, pp. 612-617.

Camarasa, et al., *J. Med. Chem.*, vol. 28, 1985, pp. 40-46.

International Publication No. WO 89/12062, Dec. 14, 1989.

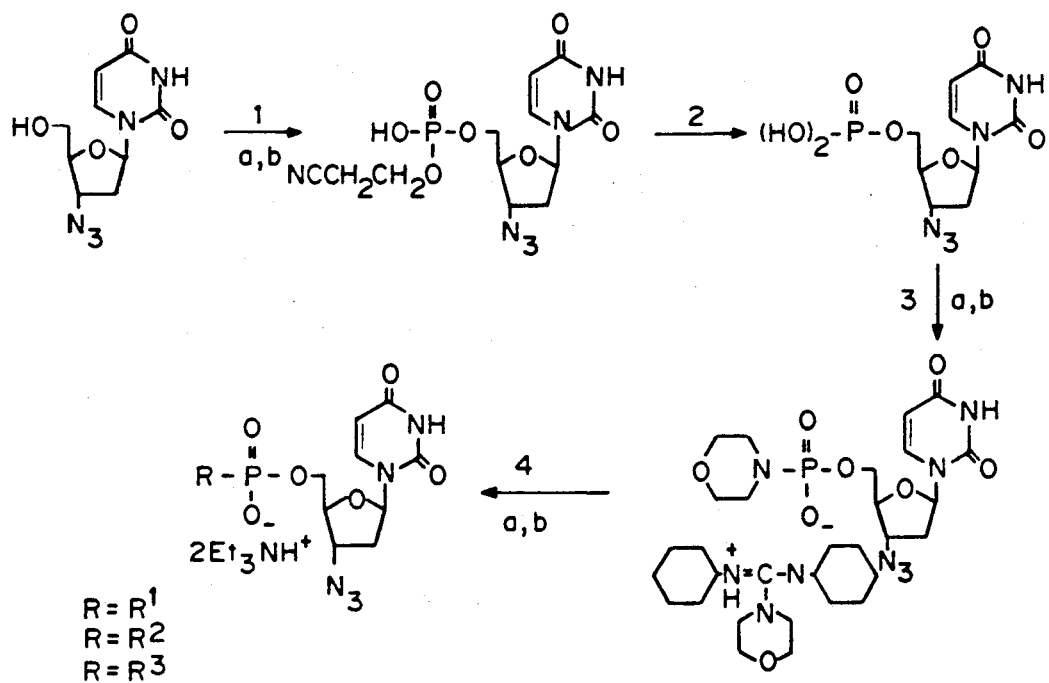
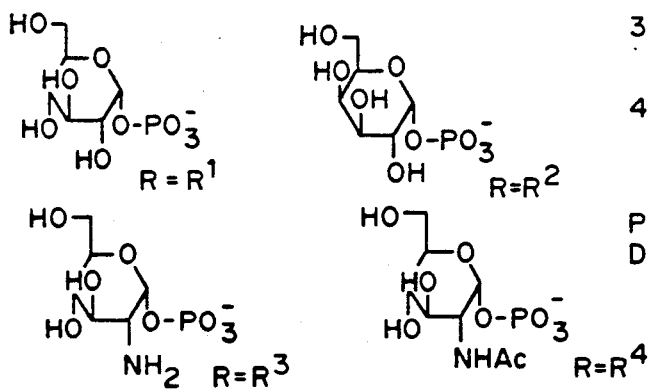
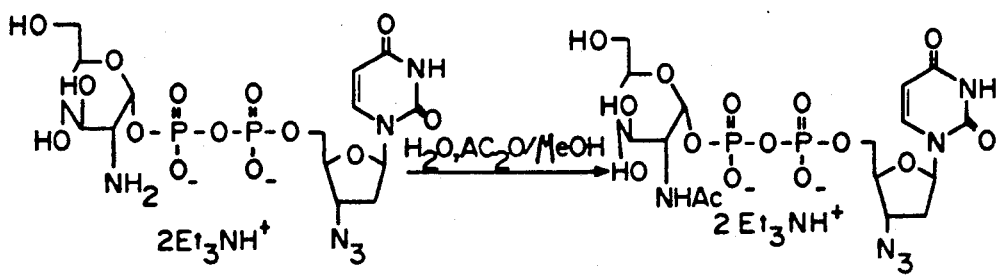
FIGURE 2
1. a = NCCH₂CH₂OPO₃(Py)₂
   b = DCC, Pyridine
2. Aq KOH, 100° C 15 Min.
3. a = morpholine, tert butanol H₂O
   b = DCC
4. a = R¹, R² or R³ as their trioctyla-
   mine salt, Pyridine
   b = sodium acetate
Py = Pyridine
DDC = Dicyclohexylcarbodiimide

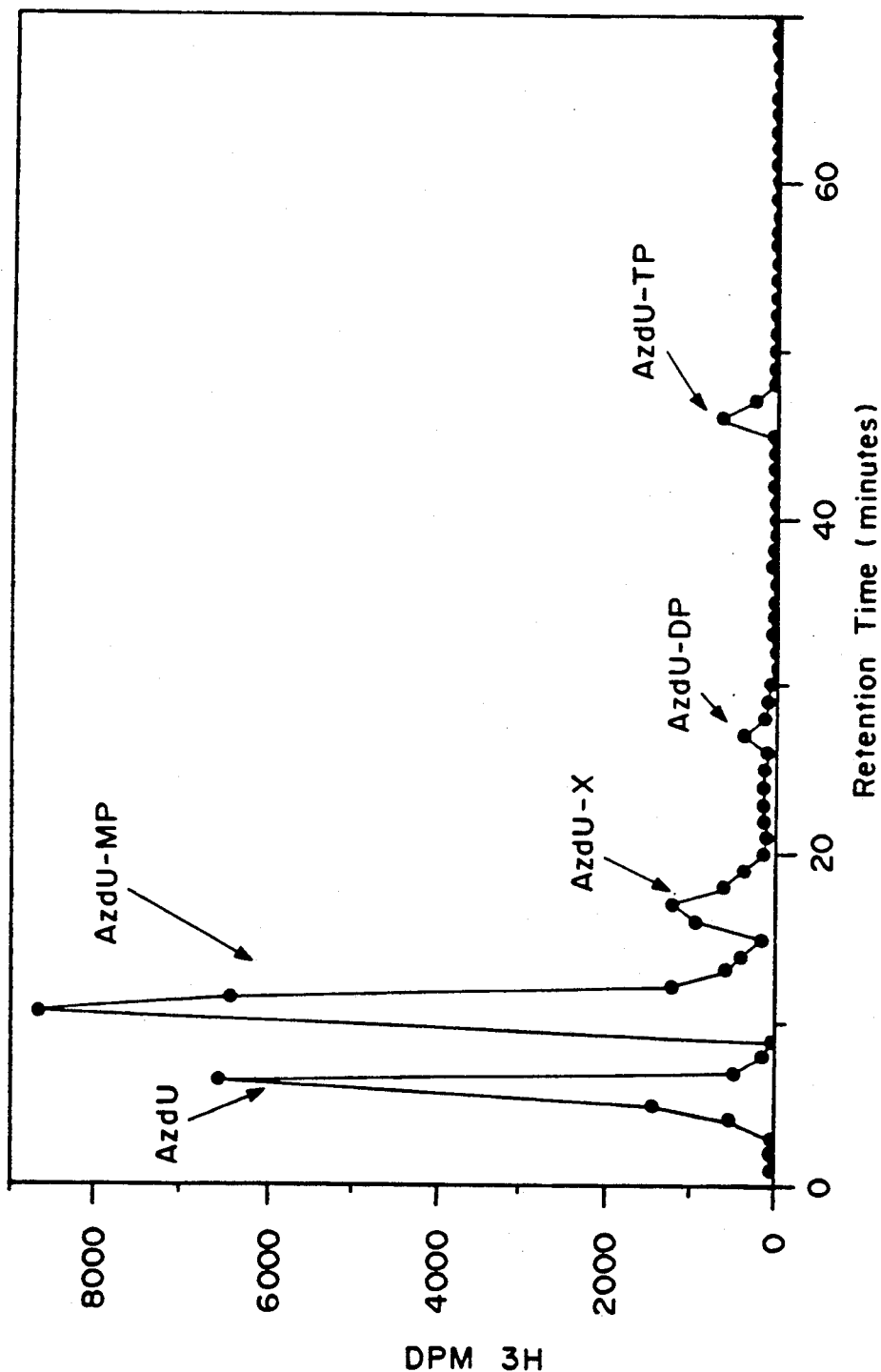

A novel pathway which traps AzddU intracellularly

5'-DIPHOSPHOHEXOSE NUCLEOSIDE PHARMACEUTICAL COMPOSITIONS

The U.S. Government has rights in this invention as a result of the financial assistance of Veteran Affairs Merit Review Awards and grants from the National Institute of Health.

This is a Continuation-in-Part of U.S. Ser. No. 07/377,617, entitled "5'-Diphosphohexose Nucleoside Pharmaceutical Compositions", filed Jul. 10, 1989, by Raymond F. Schinazi, Jean-Pierre Sommadossi, and Chung K. Chu, which is a Continuation-in-Part of U.S. Ser. No. 07/104,438, which issued on Apr. 10, 1990, as U.S. Pat. No. 4,916,122, entitled "3'-Azido-2',3'-Dideoxyuridine Antiviral Compositions," filed Oct. 2, 1987, by Chung K. Chu and Raymond F. Schinazi, which is a Continuation-in-Part of U.S. Ser. No. 07/007,473, now abandoned, entitled "3'-Azido-2',3'-Dideoxypyrimidines and Related Compounds as Antiviral Agents" filed Jan. 28, 1987 by Chung K. Chu and Raymond F. Schinazi. U.S. Ser. Nos. 07/377,617, 07/104,438 and 07/007,473 are incorporated herein by reference.

TECHNICAL FIELD OF INVENTION

The present invention is in the pharmaceutical area, and in particular relates to pharmaceutical compositions containing 5'-diphosphohexose and 5'-diphosphohexosamine nucleoside derivatives.

BACKGROUND OF THE INVENTION

Acquired immunodeficiency syndrome ("AIDS") was recognized as early as 1979. The number of cases reported to the Centers for Disease Control (CDC) has increased dramatically each year since then, and in 1982 the CDC declared AIDS a new epidemic. Infection with the AIDS virus is highly variable. Initially, the virus replicates abundantly, with virus present in the central nervous system and the cells of the immune system. This is frequently accompanied by fevers, rashes, flu-like symptoms and neurological complaints. These symptoms generally disappear within a few weeks, as the amount of virus in the circulation drops. However, virus is still present in the immune cells, the cells of the nervous system, cells of the intestine, and in bone marrow cells. The victim typically dies two to ten years after the initial asymptomatic period, following a protracted and painful illness.

Human immunodeficiency virus (HIV), a retrovirus, has been determined to be the etiological agent of AIDS, as well as of a variety of related disorders, such as AIDS Related Complex (ARC) (see, e.g., Barré-Sinoussi, F., et al., *Science* 220, 868-871 (1983); Gallo, R. C., et al., *Science* 224, 500-503 (1984).

HIV infection begins when a virion or virus-infected cell binds to susceptible cells and fuses with them, injecting the core protein and viral RNA into the cell. The RNA is transcribed to viral DNA. The double stranded DNA migrates to the nucleus and is suspected to integrate into the cell's DNA. The viral DNA can remain dormant for an indefinite period of time, or the genes can replicate and be translated into viral proteins. The viral proteins are assembled into new virions that bud from the cell, spreading the disease.

HIV preferentially infects the T4 lymphocytes, immune cells that are important in helping to suppress infection in the body. As T-cells are destroyed by HIV, the body's immune system is impaired. One of the most serious complications of Acquired Immune Deficiency Syndrome is the proliferation of opportunistic infections that occur after a severe decline in immune function. "Opportunistic infection defined AIDS" is one of the final stages of the disease, typically characterized by a T4 cell count of 100 or less. Most patients die within two years of reaching this stage. The opportunistic diseases that occur most often at this stage are probably prevalent because the agents that cause them are ubiquitous in all humans, including healthy humans.

Opportunistic infections common among AIDS patients include various bacterial diseases caused by agents such as mycobacterium species (*M. avium intracellulare* and *M. tuberculosis*), Legionella sp., Salmonella sp., Shigella sp., and other bacteria that cause infections in which T-cells are important in host defense. Recently, mycoplasma bacteria have been isolated from lung biopsy tissue of HIV infected individuals. Opportunistic parasitic infections include *Pneumocystis carinii* pneumonia (PCP), toxoplasmosis (which infects the brain and leads to seizures and coma), chronic cryptococcosis (that can cause meningitis), and histoplasmosis (a frequent cause of chronic fever). An often observed secondary viral infection is cytomegalovirus, which is a cause of pneumonia, encephalitis, blindness, and inflammation of the gastrointestinal tract. This viral infection is typically a reactivation of a childhood infection that was well controlled before HIV infection. Cancers associated with AIDS include Kaposi's sarcoma, certain lymphomas, and cancer of the rectum and tongue.

A variety of approaches are being developed to treat AIDS infections. These approaches include the development of a means to inhibit the binding of the virus to host cell receptors with agents, such as dextran sulfate, or a soluble form of the CD4 receptor protein (a glycoprotein that specifically binds to the T4 receptors on the surface of certain T cells). Other approaches include the administration of anti-idiotypic antibodies (an antibody to the antibody against CD4), blockage of viral protein synthesis by compounds such as phosphorothioate, and inhibition of protein glycosylation by compounds such as 2-deoxy-D-glucose. These approaches, however, are still in early experimental phases, and have not been approved for clinical treatment.

Antiviral chemotherapy now represents the major approach in preventing and/or treating AIDS. AIDS and ARC chemotherapy has been recently reviewed by Schinazi, *Strategies and Targets for Anti-Human Immunodeficiency Virus Type 1 Therapy*, "Aids in Children, Adolescents, and Heterosexual Adults: An Interdisciplinary Approach to Prevention", (Elsvier, N.Y., 1988). See also: E. D. Clercq, *J. Med. Chem.* 29, 1561-1569 (1986); H. Mitsuya, S. Broder, *Nature* 325, 773-778 (1987); and R. Yarchoan, et al., "AIDS Therapies" *The Science of AIDS* Scientific American (W. H. Freeman and Co. N.Y. 1989).

A number of nucleoside derivatives have been found to have anti-HIV activity, including 3'-azido-3'-deoxythymidine (AZT), 2',3'-dideoxycytidine (DDC), 2',3'-dideoxyadenosine (DDA), 3'-azido-2',3'-dideoxyuridine (referred to variously as AzdU, AzddU, or CS-87), 2',3'-didehydro-2',3'-dideoxycytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-dideoxy-2-halo-$\beta$-D-arabinofuranosyl)-$N^6$-methyladenine (2'-halo-D2MeA), and N⁶-methyl-D-glycero-2',3'-dideoxyfuranosyladenosine (D₂MeA).

3'-Azido-2',3'-dideoxyuridine, AzdU, is a nucleoside analog that inhibits HIV replication in a variety of HIV-infected cells at concentrations close to or below 0.1 $\mu$M (U.S. Pat. No. 4,916,122 to Chung K. Chu and Raymond F. Schinazi; Schinazi, R. F., C. K. Chu, M. K. Ahn, and J. P. Sommadossi, *J. Cell Biochem. Suppl.* 11D, 74 (1987); Chu, C. K., R. F. Schinazi, B. H. Arnold, D. L. Cannon, B. Doboszewski, V. B. Bhadti, and Z. Gu, *Biochem. Pharmacol.* 37, 3543-3548 (1988); and Chu, C. K., R. F. Schinazi, M. K. Ahn, G. V. Ullas, and Z. P. Gu, *J. Med. Chem.* 32, 612-617 (1988)). This concentration is at least 200-fold less than that which inhibits colony formation of human bone marrow cells (BMC) (Sommadossi, J. P., Z. Zhou, R. Carlisle, M. Y. Xie, D. A. Wiedner, and M. H. el Kouni, *Pharmacol. Ther.* (1990), in press). AzdU has been found to inhibit HIV in vivo in clinical trials under the supervision of the U.S. Food and Drug Administration.

AzdU is significantly less toxic than AZT, although it is also slightly less effective at inhibiting the HIV virus than AZT in certain cells. The triphosphorylated form of AzdU, AzdU-TP, competitively inhibits HIV-RT with a $K_i$ value of 0.0059 $\mu$M and inhibits cellular DNA polymerase alpha with a value of 51.5 $\mu$M (B. F. H. Eriksson, C. K. Chu, and R. F. Schinazi, *Antimicrob. Agents Chemother.* 33, 1729-1734 (1989)). These $K_i$ values are similar to those observed with AZT-TP (Cheng, Y. C., et al. (1987)). However, the affinities of AzdU and AZT for thymidine kinase are significantly different, with catalytic efficiency values of 4.6 and 162, respectively. The data suggests that the monophosphorylation step may be of importance in the different behavior of the two drugs in vivo.

It is generally accepted that the active form of nucleosides such as AzdU, AZT, AzddMeC, D₂MeA, and DDC is the triphosphorylated derivative. Triphosphorylated deoxynucleosides appear to inhibit the replication of HIV by limiting the production of viral DNA by at least two mechanisms: competitive inhibition of reverse transcriptase and chain termination of viral DNA due to the missing 3'-hydroxyl group.

One critical factor in the ultimate therapeutic effectiveness of a nucleoside is how easily the nucleoside can enter the target cells and undergo phosphorylation by cellular enzymes. The efficiency of this process varies considerably among nucleosides. Despite the fact that triphosphorylated nucleosides may be the antivirally active form, they are not clinically useful, without modification, since they cannot pass through the cell membrane.

Not only are nucleosides phosphorylated intracellularly, they are also converted by intracellular enzymes into therapeutically less active metabolites. If the conversion rate to less active compounds is faster than the rate of triphosphorylation of the nucleoside, the pharmaceutical effectiveness of the nucleoside is diminished. For example, it is known that DDA in the triphosphate form is a potent HIV inhibitor in vitro, but in vivo the enzyme adenosine deaminase rapidly converts DDA to the less active DDI (2',3'-dideoxyinosine) before DDA can be phosphorylated. DDI-5'-monophosphate must then be converted to DDA-5'-monophosphate by cellular enzymes to restore the activity of the compound.

The therapeutic effectiveness of a drug is the determining factor in the dosage required for therapy. Nucleosides that pass through the cell membrane with difficulty or which are metabolized into less active or inactive forms in the cell must be administered in higher dosages. Unfortunately, most nucleosides are toxic to healthy uninfected cells at high dosage levels.

Certain 5'-diphosphorylated sugar metabolites of naturally occurring nucleosides play an important biological role in vivo, for example in the synthesis of oligosaccharides, polysaccharides, glycolipids, and glycoproteins, and as components of bacterial cell membranes. Endogenous sugar nucleotides include various derivatives with different sugar moieties including glucose, galactose, and N-acetyl-hexosamines (Datema, R., S. Olofsson, and P. A. Romero *Pharamacol. Ther.* 33, 221-286 (1987)). Certain nucleoside derivatives have also been found to block the glycosylation of proteins. Most, if not all, known nucleoside glycosylation inhibitors, however, show little selectivity and have low activity against viral infections.

Camarasa, et al., *J. Med. Chem.* 28, 40 (1985), reported that certain uridine 5'-diphosphoglucose analogues, 5'-O-[[[[(2",3",4",6"-tetra-O-benzyl- and 2",3",4",6"-tetra-O-benzoyl-α-D-glucopyranosyl)oxyl]-carbonyl]amino]sulfonyl]-2',3'-isopropylideneuridine (P-536), and the corresponding deisopropylidenated derivatives, show in vitro antiviral activity against herpes simplex virus type 1. It has been reported by Alarcon, et al., that P-536 has broad antiviral activity, including activity against adenovirus type 5, vaccinia virus, and poliovirus type 1. *Antimicrobial Agents and Chemotherapy* 1257, (1988). The compound was demonstrated to inhibit protein glycosylation, if added at a time when late viral proteins were being synthesized, and to inhibit the synthesis of nucleic acids and phosphorylation of nucleosides. Alcina, et al., *Antimicrobial Agents and Chemotherapy* 1412 (1988), later described that the same compound has activity against the flagellated protozoan *Trypanosoma cruzi.*

In light of the above, there is an immediate serious need for a new chemotherapeutic agent for the treatment of AIDS that can readily traverse the cell membrane and that is not rapidly metabolized to inactive or toxic metabolites before it can inactivate the virus. In addition, because the progression of AIDS is characterized by increasing susceptibility to opportunistic bacterial, fungal, parasitic, and viral infections, there is a strong need to develop a chemotherapeutic agent that is at the same time effective against at least some of these opportunistic infections.

It is therefore an object of the present invention to provide nucleoside derivatives that can easily pass through a cell membrane in the proper chemical form to perform a desired biological function, or a chemical form that can be rapidly converted in vivo into the active form, without being substantially inactivated.

It is another object of the present invention to provide new antiviral compositions that have low toxicity towards uninfected cells.

It is a still further object of the present invention to provide a method to enhance the cellular levels of nucleosides.

It is another object of this invention to provide nucleoside derivatives that are active against opportunistic infections, in particular, bacterial infections.

SUMMARY OF THE INVENTION

In one embodiment, the invention includes nonnaturally occurring 5'-diphosphohexose nucleoside derivatives of the formula (I):

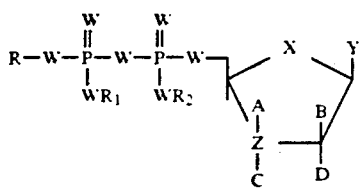

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; $R_1$ and $R_2$ are hydrogen or alkyl groups of from $C_1$ to $C_{10}$, W is oxygen or sulfur; X is oxygen, sulfur or $CH_2$; Y is a purine or pyrimidine base, Z is carbon, sulfur, or oxygen, and wherein when Z is oxygen or sulfur, A and C are not present.

Many of the unphosphorylated precursors of (I) are known compounds with known biological activity, such as anti-HIV activity (3'-azido-3'-deoxythymidine (AZT), 2',3'-dideoxycytidine (DDC), 2',3'-dideoxyadenosine (DDA), 3'-azido-2',3'-dideoxyuridine (AZddU), 2',3'-didehydro-2',3'-dideoxycytidine, 3'-deoxy-2',3'-didehydrothymidine, 3'-azido-5-methyl-2',3'-dideoxycytidine, and $N_6$-methyl-D-glycero-2',3'-dideoxyfuranosyladenosine), anti-cancer activity (9-beta-D-arabinofuranosyl-2-fluoroadenine), and anti-hepatitis and anti-herpes activity (2'-fluoro-5-ethyl-arabinofuranosyluridine). The activity of these compounds is enhanced by the addition of a diphosphohexose or diphosphohexose derivative to the 5'-position of the nucleoside. It has been discovered that these 5'-diphosphohexose derivatives pass easily through the cell membrane and are thereafter converted into the triphosphorylated derivative intracellularly. Another advantage of the derivatized nucleosides is that, after entry into cells, the 5'-diphosphohexose nucleosides do not require the initial phosphorylation by viral or cellular kinases as is necessary for activation of nonphosphorylated nucleosides. Therefore, the 5'-diphosphohexose, hexosamine, or N-acetyl aldohexosamine derivative of the nucleoside represents a new unexpectedly active precursor form of the active compounds for administration.

In a second embodiment, the invention is a pharmaceutical composition that includes an HIV-inhibitory amount of the compound of formula (I) in a pharmaceutically acceptable carrier. The composition can include other pharmaceutically active agents, and can be used in combination or alternation dose therapy with other antiviral or anti-HIV compositions.

Methods for treatment of viral or other diseases, especially AIDS or ARC, are also disclosed that include administration of an effective dose of the composition to a patient. The administration can be accomplished orally, in a controlled release device, by injection, or in combination with a liposome delivery system.

Many of the compounds of formula (I) have antibiotic activity and are, thus, useful in treating certain microbial and viral infections, including opportunistic infections that accompany HIV infection, including *M. avian ntracellulare, M. tuberculosis,* Legionella sp., *Pneumocystis carinii* pneumoniae, Salmonella sp., Shigella sp., toxoplasmosis, chronic cryptococcosis, histoplasmosis, cytomegalovirus, and members of the genus Mycoplasma. Certain compounds of formula (I) also appear to have fungal activity. This represents a significant advance in AIDS treatment in that it decreases the need to administer multiple therapies to already weakened patients.

In yet another embodiment, this invention provides antibiotically effective compositions and methods of treatment that contain at least one compound of formula (II) that is converted by eukaryotic cells into the antibiotically effective compound of formula (I).

BRIEF DESCRIPTION OF THE FIGURES

FIG. 2 is an illustration of the method of synthesis of 3'-azido-5'-O-diphosphoglucose-2',3'-dideoxyuridine, 3'-azido-5'-O-diphosphoglucosamine-2',3'-dideoxyuridine, and 3'-azido-5'-O-diphospho-N-acetylglucosamine-2',3'-dideoxyuridine.

FIG. 5 is a high performance liquid radiochromatogram of intracellular $^3H$ labeled metabolites of 3'-azido-2',3'-dideoxyuridine 24 hr after incubation of phytohemagglutinin-stimulated PBMC with 10 μM [$^3H$]AzdU.

DETAILED DESCRIPTION OF THE INVENTION

Figure 1:
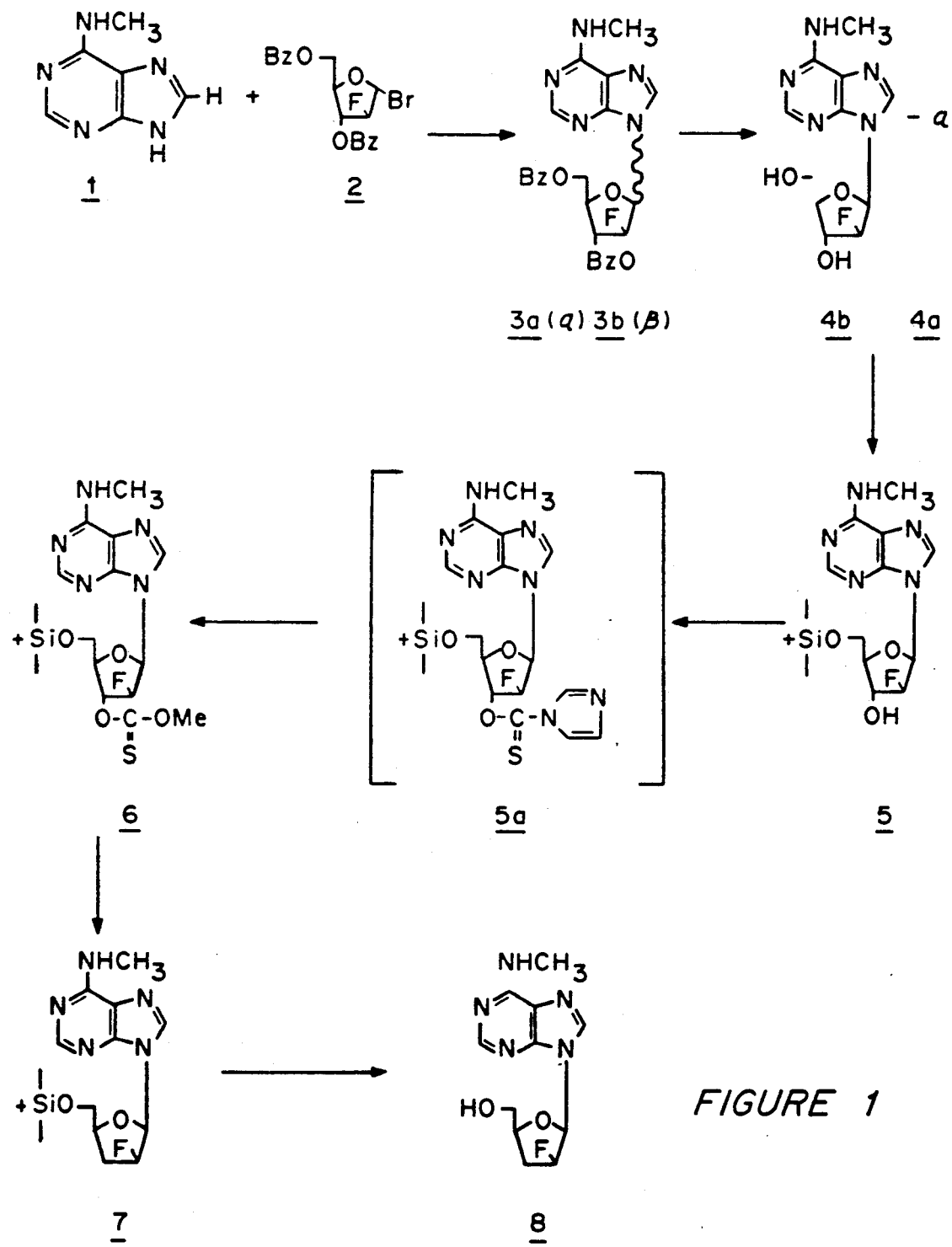
FIG. 1 is an illustration of the method of synthesis of 9-(2,3-dideoxy-2-halo-β-D-arabinofuranosyl)-$N^6$-methyladenine (2'-halo-$D_2$MeA).

Abbreviations for compounds described herein include: AzdU, 3'-azido-2',3'-dideoxyuridine; AzdU-MP, 3'-azido-2',3'-dideoxyuridine-5'monophosphate; AzdU-DP, 3'-azido-2',3'-dideoxyuridine-5'-diphosphate; AzdU-TP, 3'-azido-2',3'-dideoxyuridine-5'-triphosphate; AzdU-DP-Glc, 3'-azido-2',3'-dideoxyuridine-5'-diphosphoglucose; AzdU-DP-GlcNAc, 3'-azido-2',3'-dideoxyuridine-5'-diphospho-N-acetyl-glucosamine; AZT, 3'-azido-3'-deoxythymidine; AZT-MP, 3'-azido-3'-deoxythymidine-5'-monophosphate; AZT-TP, 3'-azido-3'-deoxythymidine-5'-triphosphate; PBMC, peripheral blood mononuclear cells; BMC, bone marrow cells; HIV, human immunodeficiency virus; AIDS, acquired immunodeficiency syndrome; RT, reverse transcriptase; HPLC, high performance liquid chromatography; and HBSS, Hank's balanced salt solution.

The term "5'-diphosphohexose nucleoside" or "5'-diphosphosugar" as used herein includes any compound of the formula (I). The term "parent nucleoside" includes any nucleoside from which the 5'-diphosphohexose nucleoside of this invention may be derived or from which it can be prepared or synthesized. Such methods of derivation, synthesis, and preparation include in vivo metabolic pathways or any methods known to those of skill in the art.

The term "antibiotically effective" refers to the ability of a compound to inhibit the growth of, or to inactivate, microorganisms, viruses or parasites that are capable of replicating in eukaryotic cells. The term "biological activity" refers to any activity of a compound that is manifested by such compound when it enters a cell or is administered to a multicellular organism. Biological activities include pharmaceutical activities. The term "pharmaceutical activity" refers to any therapeutic effect achieved by in vivo administration of a compound.

As used herein, precursors of 5'-diphosphohexose nucleosides refers to compounds that are converted by any cellular metabolic pathway, including those disclosed herein, to 5'-diphosphohexose nucleosides. Such cells may be part of a eukaryotic organism or may be cultured in vitro.

I. Preparation and Characterization of 5'-Diphosphohexose Nucleosides

In one embodiment, the invention includes nonnaturally occurring 5'-diphosphohexose nucleoside derivatives of the formula (I):

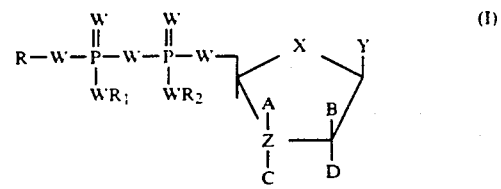

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; $R_1$ and $R_2$ are hydrogen or alkyl groups of from $C_1$ to $C_{10}$, W is oxygen or sulfur; X is oxygen, sulfur or $CH_2$; Y is a purine or pyrimidine base, Z is carbon, sulfur, or oxygen, and wherein when Z is oxygen or sulfur, A and C are not present.

Y is any purine or pyrimidine base, natural or synthetic, that combines with a sugar to form a biologically active nucleoside, such as adenine, guanine, thymine, cytosine, uracil; or derivatives thereof that have been alkylated, halogenated, haloalkylated, haloalkenylated, or hydroxyalkylated. Further, groups such as cyano, $NO_2$, $CH_2NO_2$, SH, or SW, wherein W is an alkyl group of $C_1$ to $C_{10}$ can be added to the base. The base can be attached to the sugar through a typical carbon-nitrogen bond or alternatively, through a carbon-carbon bond (forming a C-nucleoside). Methods of preparation of C-nucleosides are extensively reviewed in James, J. R, *Nucleosides and Nucleotides* 6, 417 (1979).

Z is oxygen, sulfur, or carbon. When Z is oxygen or sulfur, A and C are not present. When Z is sulfur or oxygen, cytosine or thymine, or their derivatives, are preferred Y substituents.

R is an aldohexose, aldohexosamine, or N-acetyl aldohexosamine. An aldohexose is a six carbon sugar with an aldehyde group at the end of the carbon chain, such as glucose, galactose, mannose, and fucose (6-deoxygalactose) or a modified sugar such as 2-deoxyglucose, or a halo, azido, dideoxy. or didehydro derivative of the hexose. An aldohexosamine is an aldohexose in which one of the hydroxyl groups has been replaced with an amine, such as glucosamine, galactosamine, and fucosamine.

Alternatively, a ribose, an erythrose, or a six carbon sugar without a terminal aldehyde group can be substituted for the hexose in the diphosphosugar moiety. Further, R can be an acid modified sugar such as ascorbic acid, or its imine or esterified derivative.

Examples of the compounds include, but are not limited to, the 5'-diphosphohexose, 5'-diphosphohexosamine, or N-acetyl diphosphohexosamine derivatives of 3'-fluoro-3'-deoxythymidine (FLT or FDT), 3'-fluoro-2',3'-dideoxyuridine (FDU), 3'-fluoro-2',3'-dideoxy-5-methylcytidine, 2',3'-didehydro-3'-deoxythymidine (D4T), 2',3'-dideoxyinosine (DDI), 5-E-(2-bromovinyl)-2'-deoxyuridine (BVDU) and its arabinosyl analogue (BV-ara-U), 3'-azido-3'-deoxythymidine (AZT), 2',3'-dideoxycytidine (DDC), 2',3'-dideoxyadenosine (DDA), 3'-azido-2',3'-dideoxyuridine (AzddU), 2',3'-didehydrocytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-Dideoxy-2-halo-β-D-arabinofuranosyl)-N⁶-methyladenine (2'-halo-D₂MeA), N⁶-methyl-D-glycero-2',3'-dideoxyfuranosyladenosine (D₂MeA), 9-β-D-arabino-furanosyl-2-fluoroadenine, 2'-fluoro-5-ethyl-arabino-furanosyluridine and 2'-fluoro-5-iodo-arabinofuranosyl-cytidine, and 3'-thia-2',3'-dideoxycytidine (BCH 189).

5'-Diphosphohexose and 5'-diphosphohexosamine derivatives of nucleosides can be prepared synthetically or enzymatically. In both routes, the first step involves the preparation of the unphosphorylated nucleoside. In the second step, the diphosphohexose, hexosamine, or N-acetylhexosamine is added to the nucleoside. The method of synthesis of these compounds is better understood with reference to the following nonlimiting example.

EXAMPLE 1

Synthesis of 5'-Diphosphohexose Nucleosides

A. Synthesis of Nonphosphorylated Nucleosides

Nonphosphorylated nucleosides can be prepared by methods known to those of skill in the art such as by condensing a sugar molecule with a nitrogenous base (see, for example, Dyatkina, N. B., *Soviet J. Biorg. Chem.* 12, 563 (1986); U.S. Pat. No. 4,230,689; Fleet, Son and Drome, *Tetrahedron* 44 (2), 625 (1988); Hafele and Jager, *Liebigs Ann. Chem.* 85 (1987); Baker, Joseph and Schaub, *J. Am. Chem. Soc.* 5905 (1955); Baker, Schaub and Williams, *J. Am. Chem. Soc.* 7 (1955)); or derivatizing a preformed nucleoside (see, for example, Lin, T. S. et al., *J. Med. Chem.*, 26, 544 (1983); Colla, et al. *Eur. J. Med. Chem. - Chim. Ther.* 20(4), 295 (1985); Herdewijn, et al., *J. Med. Chem.* 30, 1270 (1987); Chem Abstract 101:192378c (1984); Horowitz, et al., *J. Am. Chem. Soc.* 86, 1896 (1964); Horowitz, et al., *J. Org. Chem.* 29, 2076 (1964); Herdewijn, et al., *J. Med. Chem.* 30, 1270 (1987); Lin, et al., *Biochem. Pharmacol.* 36, 2713 (1987)).

Nucleosides with sulfur or carbon in the sugar moiety can be synthesized according to the methods known to those skilled in the art, including the methods of Y. F. Shealy, C. A. O'Dell, *J. of Heterocyclic Chem.*, 13, 1015 (1976); R. Vince, S. Daluga, *J. Med. Chem.*, 120(4), 612 (1977); and C. K. Chu, U. Reichman, V. A. Watanabe, J. J. Fox, *J. Med. Chem.*, 21, 96 (1978).

3'-Azido-2',3'-Dideoxyuridine (AzdU)

AzdU is a known compound. For the synthesis of this compound, see, for example, Lin et al., *J. Med. Chem.* 26, 1691–1696 (1983), Lin and Mancini, *J. Med. Chem.* 26, 544–548, Colla et al., *Eur. J. Med. Chem. - Chim. Ther.* 295–301 (1985). The following is a synthetic scheme for the preparation of AzdU starting from 2'-deoxyuridine.

5'-O-Trityl-2'Deoxyuridine

A solution of (50 g, 0.22 mole) of 2'-deoxyuridine and 62 g (0.22 mole) of trityl chloride in 350 ml of dry pyridine was placed in a preheated (100° C.) flask and stirred at 100° C. under air condenser for two hours. The reaction mixture was cooled to room temperature and slowly poured into 4 L of vigorously stirred ice-water. The solid obtained was filtered, washed with water until free from pyridine, and dissolved in chloroform and dried (Na₂SO₄ or MgSO₄). Filtration and evaporation of chloroform yielded the 5'-O-trityl-2'-deoxyuridine product as an syrup (96 g, 93%), which was used for the next reaction without further purification.

3'-O-Mesyl-5'-Trityl-2'-Deoxyuridine

To an ice cooled solution of 5'-O-trityl-2'-deoxyuridine (96 g, 0.2 mol) in 350 ml of dry pyridine added dropwise 70 ml of mesyl chloride (98%, sp. gr. 1480). The mixture was stirred in ice-water bath for 3 hours and poured slowly into vigorously stirred ice-water. The solid precipitated was filtered, washed with water and dried (101 g, 94%).

2,3'-Anhydro-5'-O-Trityl-2'-Deoxyuridine

3'-O-Mesyl-5'-O-trityl-2'-deoxyuridine (101 q, 0.19 mol) was suspended in 350 ml of ethanol (95%) and the mixture was heated to reflux. To the refluxing mixture was added dropwise 125 ml of an aqueous solution of sodium hydroxide (2N). The reaction mixture was concentrated under vacuum. The syrupy residue was purified by flash vacuum chromatography over a silica gel column eluting sequentially with chloroform, chloroform-methanol (50:1) and finally with chloroform-methanol (30:1). Evaporation of the pure fractions yielded 72 g (88%) of white powder, 2,3'-anhydro-5'-O-trityl-2'-deoxyuridine.

3'-Azido-5'-O-Trityl-2',3'-Dideoxyuridine

A mixture of 2',3'-anhydro-5'-O-trityl-2'-deoxyuridine (72 g, 0.165 mol) and 50 g of lithium azide in 250 ml of dry dimethylformamide was heated at 110°–120° C. for 12 hours. The reaction mixture was cooled and slowly poured into 4 L of ice-water. The solid obtained was filtered, washed with water, and dissolved in chloroform and dried (MgSO₄). Filtration and evaporation of chloroform yielded 63 g (80%) of the product as a syrup.

3'-Azido-2',3'-Dideoxyuridine (AzddU)

A mixture of 3'-azido-5'-O-trityl-2',3'-dideoxyuridine (63 g, 0.132 mol) and 300 ml of acetic acid (80%) was heated at 95°–100° C. for two hours. The reaction mixture was cooled in an ice-bath and the solid separated was filtered off. The filtrate was evaporated to dryness. The residue was dissolved in a methanol-chloroform mixture and concentrated to a syrup. The purification of the residue by flash vacuum chromatography over a silica gel column eluting sequentially with chloroform-methanol (70:1), chloroform-methanol (50:1) and finally chloroform-methanol (30:1), yielding 23 g (70%) of 3'-azido-2',3'-dideoxyuridine.

The following example describes how to prepare 9-(2,3-dideoxy-2-halo-β-D-arabinofuranosyl)-N⁶-methyladenine (2'-halo-D₂MeA). A schematic for the preparation of this compound is provided in FIG. 1.

9-(2,3-Dideoxy-2-Halo-β-D-Arabinofuranosyl)-N⁶-Methyladenine (2'-Halo-D₂MeA)

9-(2,3-Dideoxy-2-halo-β-D-arabinofuranosyl)-N⁶-methyladenine (2'-halo-D₂-halo-D₂MeA) can be synthesized from N⁶-methyladenine by the following scheme. First, the sodium salt of N⁶-methyladenine is produced in situ with NaH in anhydrous dimethyl formamide. The sodium salt of N⁶-methyladenine is then reacted with 3,5-dibenzoyl-1-bromo-2-deoxy-2-halo-α-D-arabinofuranose, which can be produced by the method of C. H. Tann et al., *J. Org. Chem.* 50, 36–44 (1985). In the method of Tann, 1,3,5-tri-O-benzoyl, 2-imidazolylsulfonylfuranose is fluorinated with KHF₂ to yield 2-deoxy-2-fluoro-1,3,5-tri-O-benzoyl-α-D-arabinofuranose, which is reacted with HBr in acetic acid to produce compound 2 (FIG. 1). Alternatively, the halogen can be added to the furanose by reaction of the 2-OH moiety with triphenylphosphine followed by $CCl_4$, $CBr_4$, or $CI_4$, at a reaction temperature of between approximately 23° C. and 60° C.

A halogen can also be added to the 2-position of the furanose ring by first reacting the 2-OH moiety with mesyl sulfonyl chloride in pyridine to form the mesylsulfonyl ester. The ester is isolated and then refluxed with KCl, NaBr, or NaI in an organic solvent such as dimethylformamide (DMF) or dimethylsulfoxide (DMSO) to form the halodeoxy sugar.

The reaction of compound 2 with the sodium salt of $N^6$-methyladenine produces a mixture of α and β anomers, 3a and 3b.

The mixture of 3a and 3b can be debenzoylated by treatment with methanol saturated with ammonia to produce 4a and 4b. The α-anomer 4a is then separated from the β-anomer 4b with flash column chromatography.

The 5'-hydroxyl group of 4b is then reacted with t-butyl-dimethylsilylchloride in DMF to form the corresponding t-butyldimethylsilyl protected nucleoside 5. The 5'-protected nucleoside 5 can be treated with excess N,N-thiocarbonyldimidazole in DMF at 80° C. for 10 hours to give intermediate imidazolides 5a, which upon reaction with methanol at 50° C. for 2 hours, yields crystalline methylthionocarbonate 6. Treatment of 6 with tri-n-butyltinhydride and triethylborane in anhydrous tetrahydrofuran under argon produces 7 in excellent yield. The final product 8 is produced by desilylation of 7 with tetrabutylammonium fluoride (TBAF) in THF at room temperature.

B. Chemical Synthesis of 5'-O-Diphosphohexose Nucleosides

5'-Diphosphohexose and 5'-diphosphohexosamine nucleosides can be prepared from the corresponding nucleoside 5'-monophosphates by reaction with dicyclohexylcarbodiimide and morpholine to form a 5'-phosphomorpholidate-4-morpholino-N,N-dicyclohexyl carboxamidium salt, which is then reacted with an α-D-sugar-1-phosphate-tri-n-octyl amine salt to form the desired product. See generally: Kochetkov, N. K. et al., *Tetrahedron* 19, 1207–1218 (1963); Tener, G. M., *J. Amer. Chem. Soc.* 83, 154 (1961); Michelson, A. M. and Todd, A., *J. Amer. Chem. Soc.* 3459 (1956); Roseman, S., Distler, J. J., Moffat, J. G. and Khorana, H. G., *J. Amer. Chem. Soc.* 83, 659 (1961); Weekbecker, G. and Keppler, D., *Analyt. Biochem.* 132, 405 (195?); and Ludwig, J. and Eckstein, F., *J. Org. Chem.* 54, 631 (1989). 5'-Diphosphohexosamines can be acetylated to the corresponding 5'-diphospho-N-acetylhexosamine according to the procedure of Weekbecker, G. and Keppler, D., *Analyt. Biochem.* 132, 405 (1957).

The following is a detailed procedure for the preparation of 3'-azido-2',3'-dideoxyuridine-5'-diphosphohexose, 3'-azido-2',3'-dideoxyuridine-5'-diphosphohexosamine as well as the corresponding N-acetyl hexosamines. The procedure is illustrated in FIG. 2.

3'-Azido-2',3'-Dideoxyuridine-5'-Monophosphate

A freshly prepared pyridinium salt of 2-cyanoethylphosphate (8.05 g, 23.64 mmol) was added to a solution of 3'-azido-2',3'-dideoxyuridine (2.50 g, 9.7 mmol) in dry pyridine (50ml) and evaporated to dryness at 30° C. The concentrated residue was dissolved in pyridine (50 ml) and the solution again evaporated to dryness. The process was repeated twice and then the residue obtained was dissolved in dry pyridine (50 ml). Dicyclohexylcarbodiimide (8.08 g, 39.1 mmol) was added to the solution. The reaction mixture was stirred for 48 hours at room temperature. Water (10 ml) was added and the solution was then filtered to remove dicyclohexylurea. The clear solution was evaporated to dryness. The residue obtained was then dissolved in 1N KOH (250 ml) and heated for 15 minutes at 100° C. The cold solution was passed through a column of acidic Dowex 50 (H−), the effluent brought to pH 9 and passed through a column of Dowex (1×4 Cl−). A linear gradient elution of 0.015N HCl to 0.15N HCl afforded 3'-azido-2',3'-dideoxyuridine-5'-monophosphate in 73% yield.

3'-Azido-2',3'-Dideoxyuridine-5'-Phosphomorpholidate

A solution of dicyclohexylcarbodiimide (2.86 g, 13.87 mmol) in t-butanol (50 ml) was added to a solution of 3'-azido-2',3'-dideoxyuridine-5'-monophosphate (1.20 g, 3.6 mmol) in $H_2O$ (36 ml) and containing morpholine (1.2 ml, 13.7 mmol) in 36 ml of t-butanol. The reaction mixture was refluxed for 1 hour and then stirring of the mixture was continued for another 18 hours. The dicyclohexylurea was then filtered off, and the solution was extracted with diethyl ether (150 ml). The aqueous phase was evaporated to dryness. The obtained residue was dissolved in methanol and then precipitated with ether to give 3'-azido-2',3'-dideoxyuridine-5'-phosphomorpholidate-4-morpholino-N,N-dicyclohexylcarboxamidinium salt (1.58 g, 68%).

3'-Azido-2',3'-Dideoxyuridine-5'-Diphosphoglucose, 3'-Azido-2',3'-Dideoxyuridine-5'-Diphosphoglucosamine, and 3'-Azido-2',3'-Dideoxyuridine-5'-Diphospho-N-Acetylglucosamine A freshly prepared α-D-sugar-1-phosphate-tri-n-octyl amine salt (2 to 3 equivalents) was added to a solution of 3'-azido-2',3'-dideoxyuridine-5'-phosphomorpholidate-4-morpholino-N,N-dicyclohexylcarbonamidinium salt in dry pyridine and evaporated to dryness. The process of dissolution in fresh dry pyridine and evaporation was repeated twice. Pyridine (dry) was added to the residue and then the solution obtained was stirred at room temperature for 42 hours. The reaction mixture was then left for 4 hours at 60° C., and the progress of reaction followed by thin layer chromatography [ethanol:$NH_4OH$:water (10:10:1)]. The solvent was then evaporated, and then water containing sodium acetate [20% more than the amount of corresponding salt was added to the mixture. The solution was extracted with ether. The combined aqueous layers were evaporated. The residue obtained was chromatographed on DEAE-Sephadex and eluted with increasing concentrations of triethyl ammonium acetate pH 4.0 (linear gradient of 0.1M buffer–1.0M buffer) to afford either 3'-azido-2',3'-dideoxyuridine-5'-diphosphoglucose, -galactose, or -glucosamine.

3'-Azido-2',3'-Dideoxyuridine-5'-Diphospho-N-Acetylglucosamine

The solution of 3'-azido-2',3'-dideoxyuridine-5'-diphosphoglucosamine (0.080 mmol) in $H_2O$ (1.0 ml) was treated with acetic anhydride (5 equivalent) (0.0408 g, 0.40 mmol) in $CH_3OH$ (0.5 ml) containing $H_2O$ (20%) at 0° C. The resulting mixture was stirred for another 18 hours at 0° C. The solution was concentrated and the residue obtained was then chromatographed on DEAE-sephadex as described above to afford 3'-azido-2',3'-dideoxyuridine-5'-diphosphate-N-acetylglucosamine (53%).

C. Enzymatic Synthesis of 5'-O-Diphosphohexose Nucleosides

5'-O-Diphosphoglucose nucleosides can be prepared from the reaction of the corresponding triphosphorylated nucleosides with glucose-1-phosphate in the presence of inorganic pyrophosphatase and bacterial diphosphoglucose-pyrophosphorylase. For example, if a 5'-O-diphosphoglucose uridine nucleoside is desired, the enzyme uridine diphosphoglucose-pyrophosphorylase is used. If 5'-O-diphosphogalactose uridine is desired, the enzyme uridine diphosphogalactose pyrophosphorylase is substituted for uridine diphosphoglucose-pyrophosphorylase. Alternatively, a 5'-O-diphosphogalactose nucleoside can be prepared by epimerization of the glucose molecule of 5'-O-diphosphoglucose uridine nucleoside by the enzyme uridine diphospho-glucose-4-epimerase. These enzymes can be commercially obtained from Sigma Chemical Company. Currently, enzymes are not available for the synthesis of 5'-O-diphospho-N-acetylhexosamine nucleosides or 5'-O-diphosphofucose nucleosides.

5'-O-Triphosphonucleoside can be prepared from the corresponding monophosphates as described by Hoard, et al., *J. Am. Chem. Soc.*, 87(8) 1785-1788 (1965). The monophosphates can be prepared by the method of Imai, *J. Org. Chem.*, 34(6), 1547-1550 (1969), or as described in Section B above.

The following example further illustrate how to prepare the 5'-O-diphosphohexose nucleosides enzymatically.

Synthesis of
3'-Azido-2',3'-Dideoxyuridine-5-O-Diphosphoglucose

To 150 milligrams of AzddU-triphosphate was added 400 milligrams of glucose-1-phosphate, 6 millimole of $MgCl_2$, 0.70 millimole of Tris-HCl pH 7.6, bacterial UDPG-pyrophosphorylase and inorganic pyrophosphatase. After 4 hours at room temperature, the reaction was stopped with perchloric acid (7N). After 30 minutes in ice, samples were centrifuged and the supernatant was neutralized with base After another 30 minutes in ice, samples were recentrifuged and Azddu-5'-diphosphoglucose was purified by column chromatography.

II. Pharmaceutical Activity of 5'-Diphosphohexose Nucleosides

A. Antiviral Activity

Many of the compounds of formula I have antiviral activity, including anti-HIV activity. In one embodiment of the method for using these compounds, an effective amount of a composition containing the active 5'-diphosphohexose nucleoside is administered to a patient needing treatment. Administration of the composition can be accomplished orally, in a controlled release device or in combination with a liposome delivery system, by injection, or by other means known to those of skill in the art, alone or in combination with other active agents.

The 5'-diphosphohexose derivatives of formula I with antiviral, and in particular, anti-HIV activity can be determined easily by testing the desired compound in the assay described in Example 2. The toxicity of the compound can be estimated with the procedure described in Example 3.

EXAMPLE 2

Anti-HIV Activity of
3'-Azido-2',3'-Dideoxyuridine-5'-Diphosphohexoses in Human Peripheral Blood Mononuclear Cells Assay A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of artiviral compounds.

B. Approximately 45 minutes after infection, medium, with the compound to be tested (2 times the final concentration in medium) or without compound, was added to the flasks (5 ml; final volume 10 ml). AZT was used as a positive control.

C. The cells were exposed to HIV (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171-183, 1985) and Spira et al. (*J. Clin. Meth.* 25, 97-99, 1987), except that fungizone was not included in the medium (see Schinazi, et al., *Antimicrob. Agents Chemother.* 32, 1784-1787 (1988)). The reverse transcriptase activity in the virus-infected control was about $2 \times 10^5$ dpm per ml. Blank and uninfected cell control values were about 300 and 1,000 dpm, respectively.

D. On day 6, the cells and media were transferred to a 15 ml tube and centrifuged at about 900 g for 10 minutes. Five ml of supernatant were removed and the virus concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

Results

The median effective ($EC_{50}$) concentrations for AzddU-5'-diphosphohexoses, as determined by the median effect method (*Antimicrob. Agents Chemother.* 30: 491-498, 1986), are shown in Table 1.

TABLE 1

ANTI-HIV-1 ACTIVITY AND TOXICITY OF AzddU-5'-DIPHOSPHOHEXOSES IN HUMAN PBM CELLS

[Structure: R—O—P(=O)(O⁻)—O—P(=O)(O⁻)—O—CH₂—(sugar ring with N₃ at 3')—N-uracil]

| R | EC$_{50}$ (μM) | IC$_{50}$ (μM) In PBM Cells |
|---|---|---|
| [hexose: HO—, OH, OH, OH] | 0.03 | >100 |
| [hexose: HO—, HO, OH] | 0.57–2.09 | >100 |
| [hexose: HO—, OH, NHAc] | 0.02–0.41 | >100 |
| [hexose: HO—, OH, NH₂] | ND | ND |

Briefly, in the median effect method, the percent inhibition of virus, as determined from measurements of reverse transcriptase, is plotted versus the micromolar concentration of compound. The EC$_{50}$ is the concentration of compound at which there is a 50% inhibition of viral replication.

The median effective concentration of AzdU-5'-diphosphoglucose against HIV in vitro is 0.03 micromolar, which is approximately 10 times lower than the value for the parent drug, AzddU. The median effective concentration of 3'-azido-2',3'-dideoxyuridine-5'-diphospho-N-acetyl-glucosamine against HIV in vitro is 0.02–0.41 micromolar, indicating that it is also a very highly potent anti-HIV agent. The median effective concentration of 3'-azido-2',3'-dideoxyuridine-5'-diphospho-N-acetyl-glucosamine in vitro is 0.57–2.09 micromolar, again, indicative of potent activity against HIV.

EXAMPLE 3

Determination of Toxicity of 3'-Azido-2,3'-Dideoxyuridine-5'-Diphosphohexoses in Peripheral Blood Mononuclear Cells.

Assay

The toxicity of the test compound was determined in mitogen-stimulated PBM cells (3.8 × 10$^5$ cells/ml) cultured in the presence and absence of the test compound under conditions similar to those used for the antiviral assay described above but without virus. The cells were counted after 6 days using a hemacytometer and the trypan blue exclusion method, as described by Schinazi et al., *Antimicrobial Agents and Chemotherapy*, 22(3), 499 (1982).

Results

The effect of the compounds on the growth of uninfected human PBM cells in culture is used as an indicator of the toxicity of the test compound to the normal viability of cells. The IC$_{50}$ is the concentration of compound which inhibits 50% of normal, uninfected, cell growth. 3'-Azido-2',3'-dideoxyuridine-5'-diphosphoglucose, 3'-azido-2',3'-dideoxyuridine-5'-diphospho-N-acetyl-glucosamine, and 3'-azido-2',3'-dideoxyuridine-5'-diphospho-N-acetyl-galactose were determined to have IC$_{50}$s of greater than 100 μM in cultured PBM cells. This indicates that these compounds have significantly low toxicity.

The therapeutic index of a compound is calculated by dividing the IC$_{50}$ for the compound by its EC$_{50}$. The therapeutic index is important because it is a measure of the margin of safety in administering a pharmaceutical composition containing the active compound. The 5'-diphosphohexose derivatives disclosed here have very high therapeutic indices.

B. Enhancement of Known Biological Activity

A method to enhance the known biological activity of a nucleoside also is provided that includes derivatizing the nucleoside to its corresponding 5'-diphosphohexose. The biological activity is enhanced at least in part by increasing the ability of the compound to pass through the cell membrane, thereby increasing the intracellular levels of the active compound. In a preferred embodiment, the intracellular levels of biologically active nucleosides are enhanced by preparing and administering the 5'-diphosphohexose, 5'-diphospho-N-acetylhexosamine or 5'-diphosphohexosamine derivative of the nucleoside.

The starting biological activity of the compound that is enhanced is generally known or can be ascertained by methods known to those of skill in the art. For example, compounds such as 3'-azido-3'-deoxythymidine (AZT), 2',3'-dideoxycytidine (DDC), 2',3'-dideoxyadenosine (DDA), 3'-azido-2',3'-dideoxyuridine (AzddU), 2',3'-didehydro-2',3'-dideoxycytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-dideoxy-2-halo-β-D-arabinofuranosyl)-N$^6$-methyladenine (2'-halo-D$_2$MeA), and N$^6$-methyl-D-glycero-2',3'-dideoxyfuranosyladenosine (D$_2$MeA) are known to possess activity against HIV. This activity is enhanced by addition of the diphosphate group in combination with the hexose or hexose derivative. 9-β-D-Arabino-furanosyl-2-fluoroadenine is an anticancer agent. 2'-Fluoro-5-ethylarabinofuranosyluridine is an antihepatitis and antiherpes agent. Many nucleosides, including some of those listed above, have antibacterial and antiparasitic activity.

As an example, as described in detail in Section B above, the anti-HIV activity the parent nucleoside, AzdU, is approximately 10 times lower than that of AzdU-5′-diphosphoglucose and 3′-azido-2′,3′-dideoxyuridine-5′-diphospho-N-acetylglucosamine. As another example, the antiviral compound carbovir is an unphosphorylated nucleoside wherein X is CH$_2$, Y is guanosine, A and B are replaced by a double bond, and C and D are hydrogens. By adding the diphosphosugar moiety in the 5′ position, as described herein, the biological activity of carbovir can be enhanced.

Figure 11:
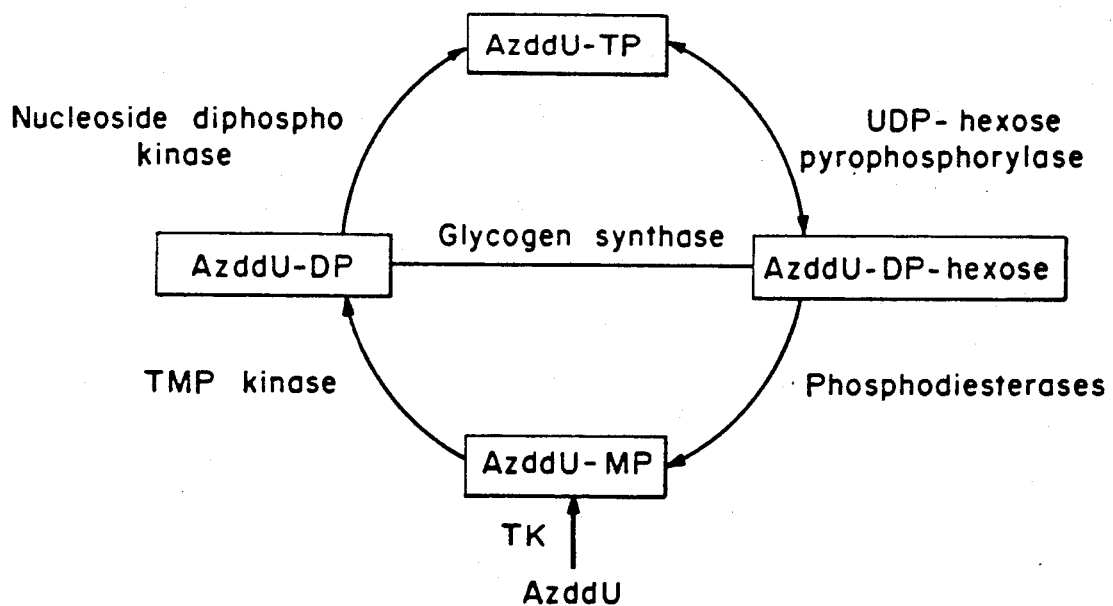
FIG. 11 is an illustration of possible metabolic pathways of 3'-azido-2',3'-dideoxyuridine.

Another advantage of the derivatized nucleosides is that, after entry into cells, the 5′-diphosphohexose nucleosides do not require the initial phosphorylation by viral or cellular kinases as is necessary for activation of non-phosphorylated nucleosides. For example, it is known that AzddU is converted by cellular kinases to AzddU-5′-monophosphate. However, the diphosphosugar analogues of AzddU do not need to be converted initially to the 5′-monophosphate. After uptake by the cells, they can be converted directly to the active antiviral compound, AzddU-5′-triphosphate. Alternatively, the diphosphosugar nucleoside can be cleaved intracellularly by phosphodiesterases to form a monophosphonucleoside, which can then be converted to the anti-virally active 5′-triphosphate nucleoside, by-passing the first phosphorylation step. See FIG. 11.

The ability of the 5′-diphosphohexose moiety to enhance the known biological activity of a nucleoside can be measured by assays such as those described above or by other in vitro or in vivo methods known to those skilled in the art.

C. Antibiotic Activity of 5′-Diphosphohexose Nucleosides

Antibacterial Activity

As discussed in the Background of the Invention, certain 5′-diphosphorylated sugar metabolites of naturally occurring nucleosides play an important biological role in vivo, for example in the synthesis of oligosaccharides, polysaccharides, glycolipids, and glycoproteins, and as components of bacterial cell membranes. Certain nucleoside derivatives have been found to block the glycosylation of proteins. Most, if not all, known nucleoside glycosylation inhibitors, however, show little selectivity and have low activity against viral infections.

It has now been discovered that certain of the 5′-diphosphohexose nucleoside derivatives disclosed here possess selective antibiotic activity. For example, the 5′-diphospho-N-acetyl-glucosamine derivative of 3′-azido-2′,3′-dideoxyuridine (AzdU-DP-N-acetyl-glucosamine), is a potent antibacterial agent as well as an anti-HIV agent. While the mechanism of action of antibiotic activity is not known, it is postulated that, in bacteria, the derivatives interfere with the biosynthesis of oligosaccharides, polysaccharides, glycolipids, or glycoproteins, or interfere with the maintenance of the bacterial cell wall through inhibitin of peptidoglycan biosynthesis.

The antibacterial activity of the 5′-diphosphohexose nucleosides can be assessed with the following assay.

EXAMPLE 4

Bactericidal properties of AzdU-DP-hexose compounds

*Staphylococcus aureus*, 8325-4, was grown to midlog phase in LB broth. Five milliliters of the midlog culture (absorption at 650 nm 0.339) was pelleted by centrifugation and the supernatant discarded. The pellet was resuspended in HBSS (pH 7.5) and the bacteria diluted to give $10^5$ colony forming units (C.F.R.) per ml. The test compounds, AzddU (3′-azido-2′,3′-dideoxyuridine), AzddU-DP-Glc, (3′-azido-2′,3′-dideoxyuridine-5′-diphosphoglucose); AzddU-DP-GlcNAc (3′-azido-2′,3′-dideoxyuridine-5′-diphospho-N-acetyl-glucosamine), AZT (3′-azido-3′-deoxythymidine) and the positive control (an antibacterial peptide) were incubated with 100 μl of the diluted culture. The compounds were added to give a final concentration of 500 μg/ml. The total reaction volume was 200 μl. The controls were prepared in the same manner except that HBSS was added instead of test compound. The mixtures were incubated for 1 hr at 37° C.

Following incubation, 100 and 10 μl of each mixture was plated onto LB agar. All plates were incubated at 37° C. for 24 hours. The number of C.F.U. was determined after incubation. The percentage of bacteria surviving was calculated with the following equation: $100 \times$ (number of C.F.U. in the presence of the test compound/number of C.F.U. in the absence of the test compound). The results are provided in FIG. 3.

Figure 3:
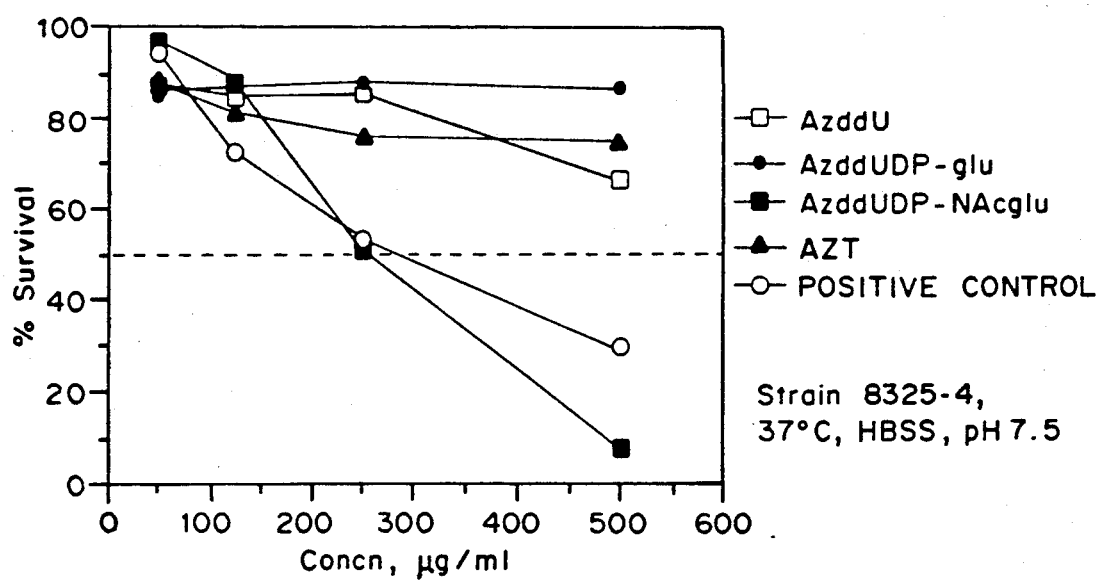
FIG. 3 is a graph of the percent survival of *S. aureus* after incubation with various concentrations (μg/ml) of 3'-azido-2',3'-dideoxyuridine (-□-), 3'-azido-5'-O-diphosphoglucose-2',3'-dideoxyuridine (-•-), 3'-azido-5'-O-diphospho-N-acetylglucosamine-2',3'-dideoxyuridine (-■-), 3'-azido-3'-deoxythymidine (-▲-), and a antibacterial peptide as a positive control (-O-) against *S. aureus*.

FIG. 3 shows that, other than the positive control, the only compound that inhibited *Staphylococcus aureus* was AzdU-DP-N-acetylglucosamine. Neither the parent compound, AzddU, nor its 5′-diphosphoglucose derivative, were active against this bacteria. AZT was also inactive against this cell line.

The kinetics of the bactericidal activity of AzdU-DP-N-acetylglucosamine was determined as follows. At midlog phase (absorption at 650 nm 0.340) a sample of a culture of *S. aureus* was diluted about $10^5$-fold and exposed to either 100 μl of AzdU-DP-N-acetylglucosamine (final concentration 500 μg/ml) or 100 μl of buffer as a control. The mixtures were incubated and 37° C. and 100 μl samples were plated at 15 minute intervals for two hours. The results are shown in FIG. 4.

Figure 4:
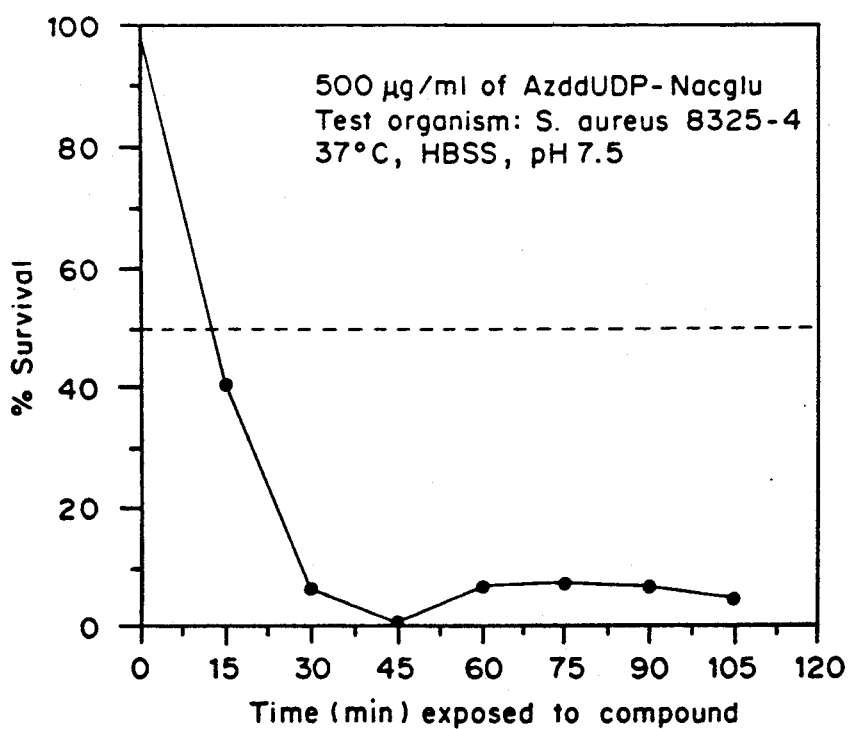
FIG. 4 is a graph of the kinetics of inactivation of *S. aureus* by 500 μg/ml of 3'-azido-5'-O-diphospho-N-acetylglucosamine-2',3'-dideoxyuridine ((-•-) AzdU-DP-NAcGlu) at 37° C. in HBSS at pH 7.5.

As shown in FIG. 4, the antibacterial activity of AzdU-DP-N-acetylglucosamine was rapid with almost complete inactivation occurring in 30 minutes.

In addition, at least $10^7$ CFU/ml of bacteria is required to overcome the effect of AzdU-DP-N-acetyl-glucosamine (500 μg/ml), indicating that this compound is a potent antibacterial compound.

Antifungal Activity

HIV-infected individuals have an increased risk of infection by certain fungi because of the substantial decrease in number of helper T cells in their immune system. Fungal agents commonly associated with HIV infection are *Candida albicans, Cryptococcus neoformans, Aspergillus* sp., and *Coccidioides immitis*. These fungi are dimorphic in that they can exist as either yeasts or molds depending on environmental conditions such as temperature and availability of nutrients. The fungal infections are often lethal. Unfortunately, there are presently only a limited number of approved anti-fungal compounds that can be offered to the infected patient.

Fungi have complex carbohydrates in their membranes. Biosynthetic pathways that incorporate N-acetylglucosamine in macromolecules required for fungal viability may be inhibited by the 5'-diphosphohexose nucleoside of formula (I). Therefore, another embodiment of this invention is the treatment of fungal infections by administration of an effective amount of a compound of formula (I) in combination with a pharmaceutically acceptable carrier.

The compounds of formula I that have fungal activity can be determined by testing the compound in a fungal assay such as that described below, or another known to those in the art.

EXAMPLE 5

Antifungal Activity of 5'-Diphosphohexose Nucleosides

The test fungus is propagated on appropriate agar containing media (Sabaroud agar) and incubated at 30° C. and 37° C. to isolate dimorphic forms. The fungi are then removed from the plates, diluted with Sabaroud broth to a concentration of $10^5$ CFU/ml, and incubated in the presence of test compounds at 30° C. and 37° C. for 1-6 hours. Controls prepared similarly but without test compound are also incubated. Viability is assessed by dilution plating onto Sabaroud agar. All plates are incubated for 48 hours prior to enumeration.

D. Biological Activity of 5'-Diphosphohexosenucleoside Precursors

It has been discovered that certain nonnaturally occurring nucleosides are converted to their corresponding 5'-diphosphohexose derivatives intracellularly. This biological pathway opens a new important means of therapy, when combined with the discovery that many of the 5'-diphosphohexose derivatives have unique biological activity such as antibacterial and antifungal activity.

Therefore, another embodiment of this invention is the selection and administration of a nucleoside of the formula (II)

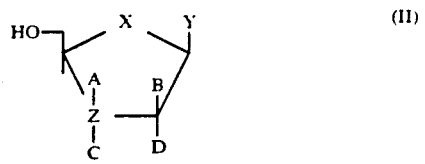

wherein A, B, and C are hydrogen, halogen, or azido; D is hydrogen, halogen, azido, or OH; A and B or C and D can be replaced with a double bond; Y is a purine or pyrimidine base, Z is carbon, sulfur, or oxygen, and wherein when Z is oxygen or sulfur, A and C are not present, in combination with a pharmaceutically acceptable carrier. The compound is administered as a precursor that is activated inside a cell to perform a desired function by conversion to the corresponding biologically active 5'-diphosphohexose derivative.

For example, it has now been discovered that AzddU is converted to the corresponding 5'-diphospho-N-acetylglucosamine derivative in certain human cells. It has also been discovered that the N-acetylglucosamine derivative is a potent antibacterial agent. Therefore, the parent compound can be administered as a prodrug, or precursor, that is converted intracellularly to an antibacterial agent capable of killing bacteria inside the cell. It is known that bacteria are capable of existing within a variety of cells, including PBM cells, bone marrow cells, and macrophages.

Further, as stated above, AzdU exhibits anti-HIV activity in vivo, and is now in clinical trials under the supervision of the FDA. As disclosed here, AzdU diphosphohexose derivatives have been identified in human peripheral blood mononuclear cells as metabolites of AzdU. These metabolites can serve as prodrugs of AzdU to generate AzdU-mono-or diphosphate, thereby bypassing the nucleoside kinase needed to phosphorylate AzdU.

Certain nucleosides are not converted to the corresponding 5'-diphosphohexose intracellularly, and therefore cannot be administered as precursors for biologically active 5'-diphosphohexose nucleosides. Instead, the 5'-diphosphohexose derivative of the nucleoside must be administered directly. For example, AZT is not converted to a 5'-diphosphohexose derivative in human cells. It is also known that 3'-azido-2',3'-dideoxy-5-methylcytidine is not converted to the 5'-diphosphohexose nucleoside in monkey cells.

However, as described in more detail below, 2'-deoxyuridine (dUrd) is converted in part to the corresponding diphosphohexose nucleoside in human PBM cells. In fact, there may be a biological preference for the conversion of uridine nucleosides to 5'-diphosphohexoses, but not other nucleosides. AzdU and dUrd, at concentrations of about 2 μM in medium for 24 hr, lead to the formation of similar levels of AzdU-TP and dUrd-TP, respectively. The intracellular level of AzdU-DP-hexoses, however, are approximately 10-fold higher than the intracellular levels of dUrd-DP-hexoses. It appears that AzdU-TP is a favored substrate in reactions catalyzed by UDP-Glc and UDP-GlcNAc pyrophosphorylases.

The discovery that AzdU is extensively converted to AzdU-DP-Glc and AzdU-DP-GlcNAc intracellularly suggests a mechanism for the anti-HIV activity of AzdU other than inhibition of viral DNA synthesis by AzdU-TP. AzdU 5'-diphosphohexose may interfere with enzymes involved in the formation of HIV glycoproteins.

AzdU has extremely low toxicity in bone marrow cells. It appears that the low toxicity is the result of the major conversion of AzdU-TP to the 5'-diphosphohexose derivatives, which in turn decreases the incorporation of AzdU into host cell DNA. AzdU-5'-diphosphohexose may also serve as a depot for slow release of AzdU-TP after administration of AzdU; thus minimizing its toxicity while maintaining adequate AzdU-TP levels necessary for its anti-HIV activity. Since AZT is not converted to the non-toxic 5'-diphosphohexose derivatives in vivo, the administration of AZT results in accumulated pools of toxic AZT-TP in the cell.

The detailed cellular metabolic studies of AzdU described herein also demonstrate that AzdU-MP is not converted to AZT-MP in human PBMC and BMC, indicating that AzdU is not a prodrug of AZT but rather a unique anti-HIV agent with cellular and kinetic properties different from AZT.

Described below is a means to determine whether a compound within formula II is converted to its 5'-diphosphohexose derivative in human PBM cells. The same assay can be used to determine if the derivative is formed in other human cells by substituting another primary human cell line, for example, human macrophages. If the derivative is made in the target cell line, then the derivative can be analysed for biological activity by methods known to those skilled in the art, including methods described herein.

Example 6 provides a detailed description of the method of isolation of radiolabeled 5'-diphosphohexose metabolites of AzdU from human peripheral blood mononuclear cells incubated with radiolabeled AzdU. Example 7 provides a detailed description of the method of isolation of radiolabeled 5'-diphosphohexose derivatives of 2'-deoxyuridine from human peripheral blood mononuclear cells incubated with radiolabeled dUrd.

EXAMPLE 7

Cellular metabolism of 3'-Azido-2',3'-dideoxyuridine with formation of 5'-o-Diphospho-hexose Derivatives by Previously Unrecognized Metabolic Pathways for 2'-Deoxyuridine analogs.

AzdU, AZT, and their phosphorylated derivatives were synthesized as described in Lin, et al., *Biochem. Pharmacol.* 36, 2713 (1987), Chu, et al., *J. Med. Chem.* 32, 617 (1989), and in U.S. Pat. No. 4,916,122 to Chu et al.. Purity of the compounds was established by reverse-phase and anion-exchange high performance liquid chromatography as well as by spectrophotometric analysis. [Methyl-$^3$H]AZT (3 Ci/mmol), [5-$^3$H]AzdU (22 Ci/mmol), [2-$^{14}$C]AzdU (56 mCi/mmol), and [5-$^3$H]dUrd (20 Ci/mmol) were purchased from Moravek Biochemicals (Brea, Calif.). D-[1-$^{14}$C]-Glc (55 mCi/mmol) and [1-$^{14}$C]Glc 1-P were obtained from ICN Biochemicals Inc. (Irvine, Calif.). The purity of all radiolabeled compounds used were greater than 99% as ascertained by HPLC techniques described below. Glc 1-P, UDP-Glc, UDP-Gal, UDP-GalNAc, UTP, UDP-GlcNAc, venom phosphodiesterase I type VI, 5'-nucleotidase, UDP-Glc pyrophosphorylase (EC 2.7.7.9), and inorganic pyrophosphatase were purchased from Sigma Chemical Co. (St. Louis, Mo.). All other chemicals and reagents were of the highest analytical grade available.

Preparation of Human Primary Cells

Human rib specimens, obtained during thoracic surgery according to a protocol approved by the Institutional Review Board Committee at the University of Alabama at Birmingham, were the source for bone marrow cells. Cells were flushed from the ribs, under sterile conditions, with HBSS containing phenol red, 10% fetal calf serum, and 1% penicillin-streptomycin. The cell suspension was centrifuged at 1200 rpm in a Beckman GPR centrifuge for 10 minutes and the supernatant was discarded. After resuspension in HBSS, cells were gently layered onto 10 ml of Ficoll-Hypaque (Sigma, St. Louis, Mo.) and were centrifuged at 1500 rpm for 35 minutes. The mononuclear cell layer was removed and washed twice with HBSS. Cells were counted using a hemacytometer and viability was greater than 98%, as assessed by trypan blue exclusion. Under these condition, approximately $4 \times 10^8$ cells/rib were collected. PBMC were obtained from the whole blood of healthy HIV- and hepatitis B virus-seronegative volunteers and collected by single-step Ficoll-Hypaque discontinuous gradient centrifugation as described above. Cells were then stimulated for 3 days by 6 µg/ml of phytohemagglutinin.

Incubation Conditions and Extraction of Intracellular $^3$H

Human PBMC and BMC ($2 \times 10^6$ cells/ml) were suspended at 37° C. in a 5% $CO_2$ incubator in RPMI 1640 and McCoy's 5A media, respectively. The media was supplemented with nutrients and 15% dialyzed heat-inactivated fetal bone serum. The experiments were initiated with addition of 2 or 10 µM of [5-$^3$H]AzdU (specific activity of 400 or 200 mCi/mmol, respectively). The cells were exposed to drug for varying time periods. Cell viability was 98% or greater as assessed by trypan blue exclusion and cell number was constant for over 48 hours.

At specified time periods, $2 \times 10^7$ cells were removed and washed three times with cold phosphate-buffered saline. Extraction of cell pellets was performed overnight at $-20°$ C. with 1 ml of cold 60% methanol. After centrifugation at $15,000 \times g$ in an Eppendorf model 5414 microcentrifuge for 1 minute, the supernatant was concentrated to dryness at room temperature under a gentle stream of nitrogen. The residue was dissolved in 250 µl of distilled water and 200 µl aliquots were analyzed by liquid chromatography.

Analysis of [$^3$H]AzdU Metabolites by HPLC

A high performance liquid chromatograph (Hewlett-Packard 1090) equipped with automatic injector, filter spectrophotometric detector, and chromatographic terminal (Hewlett-Packard 3393A) was used for analysis of AzdU metabolites. The absorbance was recorded at 254 nm. Analyses were performed by three distinct methods.

System A included anion-exchange chromatography using a Partisil 10 SAX column $4 \times 250$ mm (Whatman, Inc. Clifton, N.J.) as stationary phase and a potassium phosphate buffer linear gradient as the mobile phase. The gradient started at 10 minutes. Under these conditions, the retention times of the unlabeled markers, AzdU, AzdU-MP, AzdU-DP and AzdU-TP, were 5.2, 10.8, 27.2 an 46.4 minutes, respectively.

System B was developed to separate nucleosides, nucleotides, and carbohydrate derivatives. The extracts from cells were examined using a 5 µm Apex I Carbohydrate reverse phase column ($4 \times 250$ mm, Jones Chromatography, Littleton, Colo.). The elution was carried out isocratically at 1 ml/min with 43 mM potassium phosphate buffer (pH = 2.8)/acetonitrile (77/23, v/v) and 0.09% (v/v) triethylamine. Under these conditions the retention times of the unlabeled markers, AzdU, AzdU-MP, GlcNAc, GlcNAc 1-P, UDP-GlcNAc, UDP-GalNAc, UDP-Glc and UDP-Gal were 3.5, 5.5, 7.6, 11.1, 23.9, 26.6, 29.5, and 31.9 minutes, respectively. The di- and tri-phosphate derivatives of AzdU were strongly retained using this carbohydrate column. AzdU-DP and AzdU-TP were eluted with retention times of 53 and 62 minutes, respectively, using a 10 minute linear gradient of 1M potassium phosphate buffer (pH = 2.8) and 0.09% of triethylamine from 0 to 20% starting at 35 minutes followed by a 20 minute-linear gradient of the same buffer from 20 to 80%.

System C was developed to evaluate whether AzdU-MP is converted to AZT-MP within cells. The stationary phase was identical to that of system B and elution was performed at 0.5 ml/min isocratically with a mixture of potassium phosphate buffer (pH = 2.8)/acetonitrile/triethylamine (77/23/0.09, v/v/v) and 1M potassium phosphate buffer (pH = 2.8) with 0.09% triethylamine (10/90, v/v). The retention times of AzdU, AzdU-MP, and AZT-MP were 4, 58, and 54 minutes, respectively.

For all analyses, timed fractions of 0.5 or 1 ml were collected into miniscintillation vials and radioactivity was measured using a Beckman LS-6801 liquid scintillation counter equipped with an automatic quench compensation program.

Identification of AzdU Metabolites

Initial studies in which human primary cells in suspension were exposed to [$^3$H]AzdU at various concentrations were analyzed using HPLC system A. A peak of radioactivity at 18 minutes (referred to here as AzdU-X) on the HPLC radiochromatogram was found that did not correspond to the retention time of any known phosphorylated metabolite. The following methods were used for identification of AzdU-X.

Incubation with Alkaline Phosphatase

A total of approximately 5,000 dpm of AzdU-X was isolated by HPLC and incubated with 0.31 Units of alkaline phosphatase containing 50 mM potassium phosphate buffer and 1 mM ZnSO$_4$ (pH 6.5) for 4 hours at 37° C. (total volume 150 μl). Reaction was terminated by adding 30 μl of cold 50% trichloroacetic acid. After 30 minutes at 4° C., samples were centrifuged for 1 minute at 15,000 g in an Eppendorf model 5414 microcentrifuge. The supernatant was neutralized with 60 μl of 5M potassium bicarbonate and an aliquot was analyzed by HPLC system A. Control incubations were performed with heat-inactivated enzyme.

Incubation with 5'-phosphodiesterase

Incubation conditions similar to that described above were used except that 0.048 U/ml (2 mg/ml) of venom phosphodiesterase was substituted for alkaline phosphatase.

Exposure of human primary cells to [$^3$H]AzdU and D-[1-$^{14}$C]Glc

Cells were incubated simultaneously with 2 μM [$^3$H]AzdU (specific activity, 400 mCi/mmol) and 2.5 μCi/ml of D-[1-$^{14}$C]Glc for 24 hours under identical conditions described above. As a control, cells were incubated with 2.5 μCi/ml of D-[1-$^{14}$C]Glc alone. Extraction procedures and HPLC conditions (system A) were similar to those described above.

Enzymatic synthesis of [$^{14}$C]AzdU-DP-Glc

To 150 μl of AzdU-TP (final concentration 0.1 mM) were added 25 μl of 50 mM Glc 1-P (final concentration 2.5 mM), 3.1 μCi of D-[1-$^{14}$C]Glc 1-P, 15 μl of 0.2M MgCl$_2$ (final concentration 6 mM), 50 μl of 0.67M Tris-HCl pH=7.6 (final concentration 67 mM), 5 U of bacterial UDP-Glc pyrophosphorylase, and 2 U of inorganic pyrophosphatase in a total volume of 0.5 ml. The reaction was started by addition of UDP-Glc pyrophosphorylase. After 4 hours at room temperature, the reaction was stopped with 36 μl of 7N perchloric acid. After 30 minutes on ice, samples were centrifuged and supernatant was neutralized with 240 μl of 5M potassium bicarbonate. After 30 minutes in ice, samples were re-centrifuged and an aliquot was analyzed by HPLC using system A. A negative control was performed with heat-inactivated enzyme. A positive control reaction, containing 0.1 mM of UTP in place of AzdU-TP, yielded UDP-Glc.

Results

HPLC Analysis of Intracellular $^3$H Following Exposure of Human PBMC and BMC to [$^3$H]AzdU FIG. 5 is a high performance liquid chromatogram of intracellular $^3$H metabolites 24 hr after incubation of phytohemagglutinin-stimulated PBMC with 10 μM [$^3$H]AzdU. The parent drug was phosphorylated within cells to its mono-, di- and triphosphates with retention times identical to those of authentic, chemically synthesized, AzdU nucleotide derivatives. An additional radioactive chromatographic peak (referred to as "AzdU-X") appeared with a retention time of approximately 18 minutes, using HPLC system A. This peak did not coelute with any of the known metabolites of AzdU.

A similar pattern of AzdU metabolism with formation of this unknown metabolite, which eluted between AzdU-MP and AzdU-DP, was observed in human BMC. Only minimal amounts of this metabolite could be detected in U937 and CEM-established cell lines, however, unlike in PBMC and BMC, and only after exposure of these cells to 10 μM AzdU (specific activity, 400 mCi/mmole) (see, e.g., Eriksson, B. F. H., B. J. Oswald, J. P. Sommadossi, C. K. Chu, G. Williams, R. F. Schinazi (1989) in *Vth International. Conference of AIDS, June 4-9th, Montreal, Canada*. International Development Research Center, Ontario, Canada, 152).

Characterization of "AzdU-X"

Figure 6A:
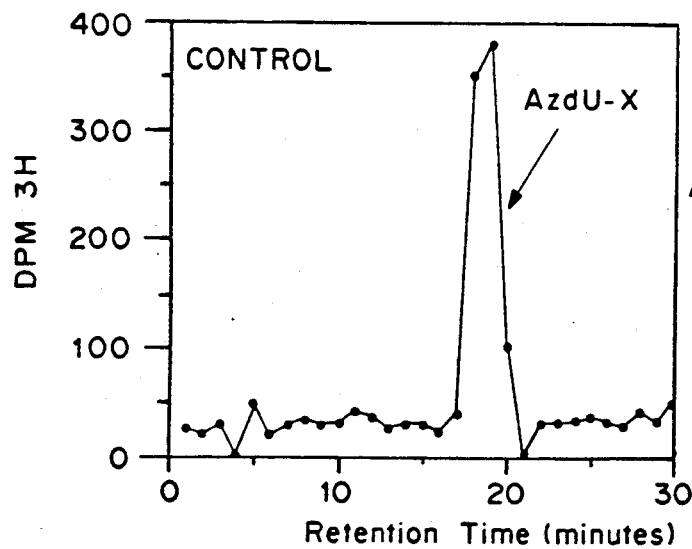
FIG. 6 is a series of high performance liquid chromatograms of peak "AzdU-X" after incubation in the presence of heat-inactivated enzyme (A), alkaline phosphatase (B), and 5'-phosphodiesterase (C). "AzdU-X" was treated for 4 hours at 37° C. with hydrolyzing enzymes and aliquots were analyzed using HPLC system A.
Figure 6B:
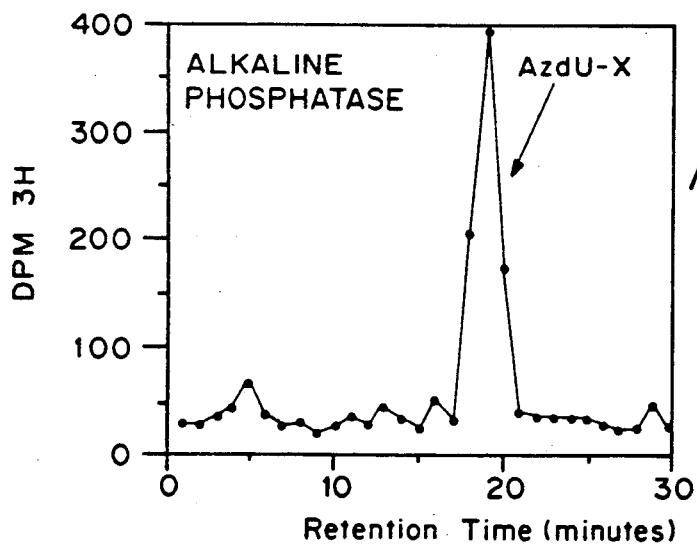
Figure 6C:
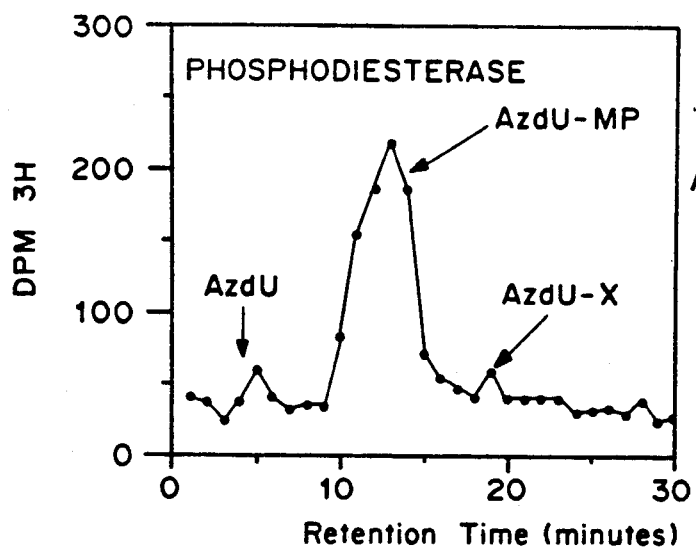

In order to identify the unknown AzdU metabolite, approximately 5000 dpm of [$^3$H]AzdU-X was isolated by HPLC and aliquots were treated with either alkaline phosphatase or venom phosphodiesterase. FIG. 6 is a series of high pressure liquid chromatograms of peak "AzdU-X" after incubation in the presence of heat-inactivated enzyme (A), alkaline phosphatase (B), and 5'-phosphodiesterase (C). "AzdU-X" was treated for 4 hours at 37° C. with hydrolyzing enzymes and aliquots were analyzed using HPLC system A. This metabolite was found to be resistant to alkaline phosphatase under conditions where 5'-phosphorylated derivatives of AzdU were readily hydrolyzed to the nucleoside. In contrast, after incubation with 5'-phosphodiesterase, essentially all the radioactivity present in the metabolite fraction was converted to AzdU-MP (FIG. 6C), indicating that a phosphodiester linkage was present in the AzdU-X structure.

To determine if the metabolite was the diphosphohexose derivative, human PBMC were incubated for 24 hr with 2 μM [5-$^3$H]AzdU (400 mCi/mmole) and D-[1-$^{14}$C]-Glc (2.5 uCi/ml). Using HPLC system A, cell extracts were found to contain a double-labeled chromatographic peak with the same retention time as AzdU-X. This supports the hypothesis that this unknown metabolite was a sugar nucleotide derivative. This peak of radioactivity was not detected when D-[1-$^{14}$C]-Glc was incubated alone.

Figure 7:
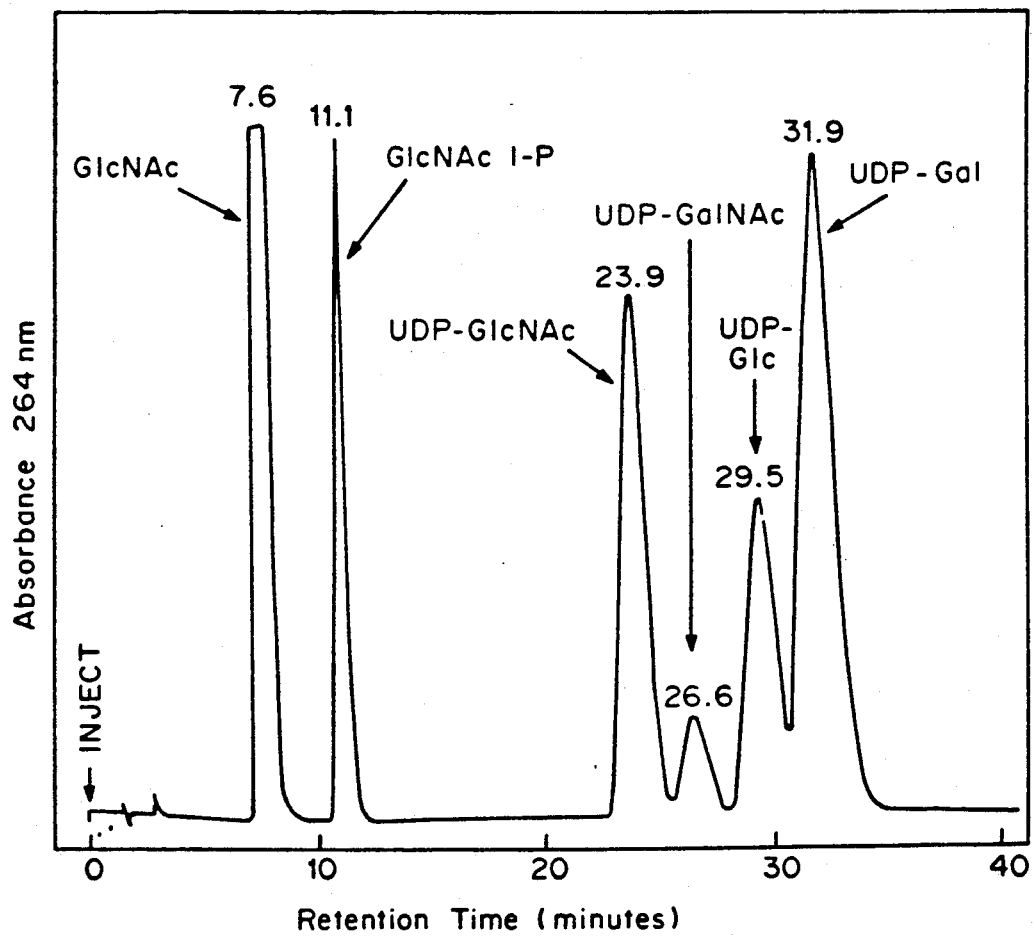
FIG. 7 is a high pressure liquid chromatogram of unlabeled authentic carbohydrates and UDP-hexose derivatives mixed standards resolved using HPLC system B. UV absorbance was monitored a 254 nm.

Based on these data and the susceptibility of the metabolite to venom phosphodiesterase but not alkaline phosphatase, the metabolite was characterized as the diphospho-hexose derivative of AzdU. In order to ascertain whether the AzdU-DP-hexose derivative, which was detected at 18 min using the HPLC system A, was a sole metabolite or the sum of several metabolites unseparated using these conditions, a new and highly specific HPLC methodology (system B) was developed to resolve nucleoside, nucleotide, and carbohydrate derivatives. FIG. 7 is a high performance liquid chromatogram demonstrating separation of various carbohydrates and Urd sugar nucleotides. The R values between UDP-Glc and UDP-GlcNAc as well as between UDP-Gal and UDP-GalNAC were identical (0.8). These products were used to develop this novel HPLC method since their chromatographic behavior was the closest to AzdU-X.

Figure 8A:
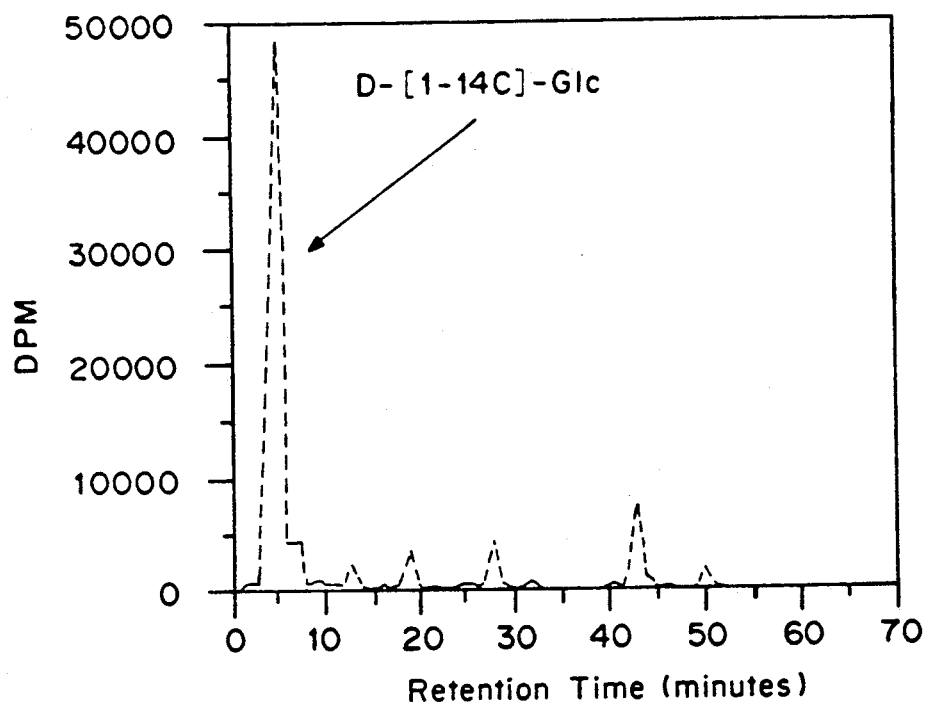
FIG. 8 is a HPLC radioactivity elution profile of a cell extract of human PBMC. $2 \times 10^7$ cells were exposed for 24 hours with D-[1-$^{14}C$]Glc alone (A) or in the presence of 2 μM [$^3H$]AzdU (B). Extracts were analyzed by HPLC system A. Radioactivity derived from $^{14}C$ and $^3H$ is represented by a dotted line and a solid line, respectively.
Figure 8B:
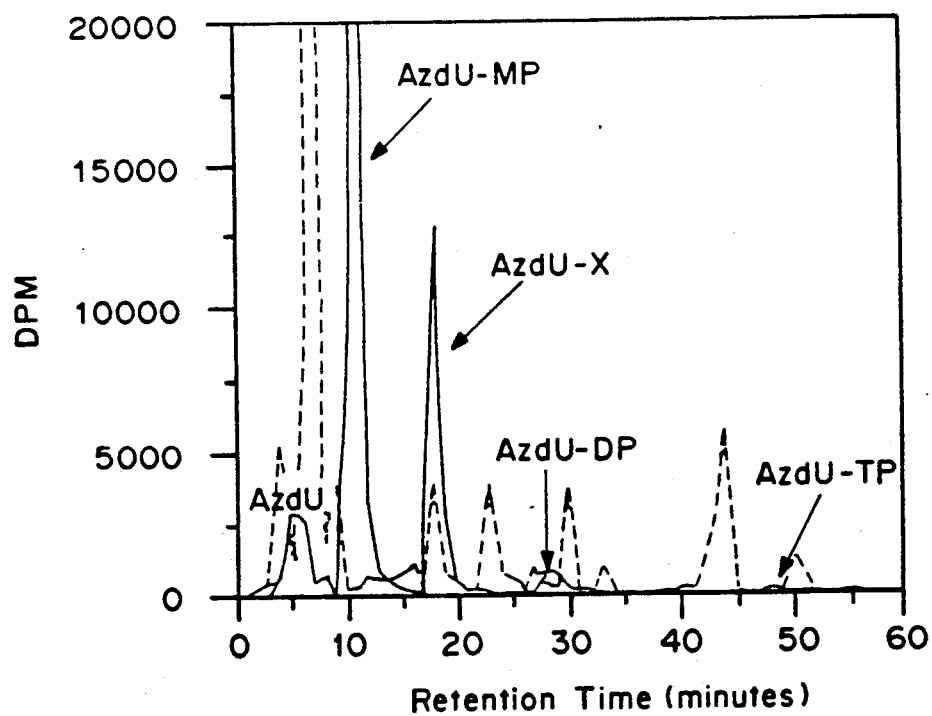
Figure 9:
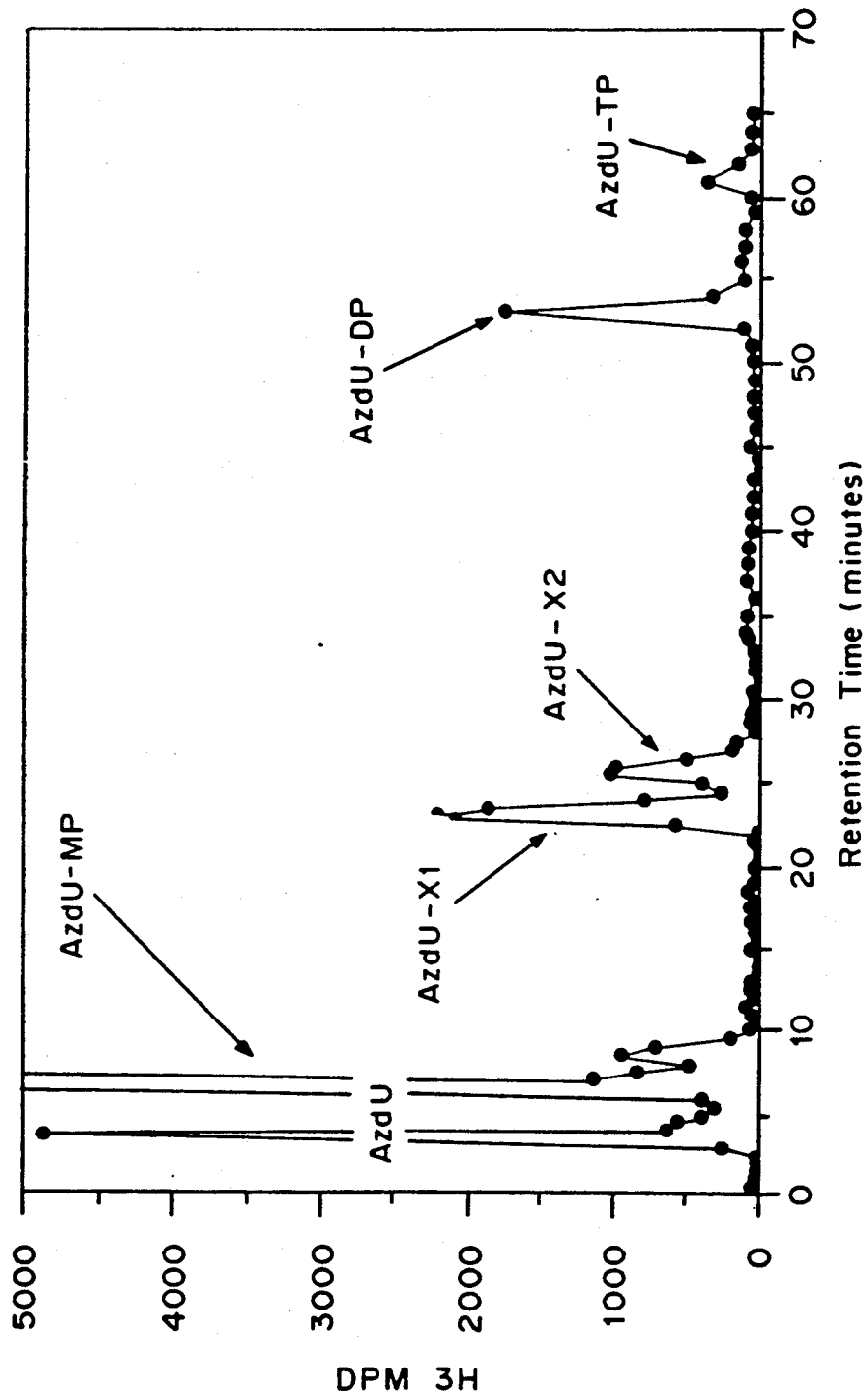
FIG. 9 is a HPLC of AzdU metabolites in human PBMC by using system B. Timed fractions of 0.5 ml were collected after 65 minutes Retention times are indicated on the abscissa.

Using HPLC system B, a portion of the cell extract analyzed above was injected and timed fractions of 0.5 ml were collected over 65 minutes. FIG. 8 is a HPLC radioactivity elution profile of a cell extract of human PBMC. $2 \times 10^7$ cells were exposed for 24 hours with D-[1-$^{14}$C]Glc alone (A) or in the presence of 2 $\mu$M [$^3$H]AzdU (B). Extracts were analyzed by HPLC system A. Radioactivity derived from $^{14}$C and $^3$H is represented by a dotted line and a solid line, respectively. As shown, under the system B conditions, the AzdU-X eluted as two chromatographic peaks (to be referred to as AzdU-$X_1$ and AzdU-$X_2$) with retention times of 23 and 26 mins. (FIG. 7). The R value between the AzdU-$X_1$ and AzdU-$X_2$ was approximately 0.8, suggesting that these metabolites could represent the dP-hexose and the dP-N-Acetyl-hexosamine derivative of AzdU. The cellular synthesis of UDP-Glc is a cytoplasmic process with UDP-Glc pyrophosphorylase catalyzing the synthesis of UDP-Glc from UTP and Glc-P. The formation of UDP-Gal however, is mediated from UDP-Glc either by Gal 1-P uridyl transferase (EC 2.7.7.12), or UDP-GAL 4.-epimerase (EC 5.1.3.2) (Keppler, D. O., and A. Holstege. "Pyrimidine nucleotide metabolism and its compartmentation", in Metabolic Compartmentation (H. Sies, ed.). Academic Press, New York, 147–203. (1982)).

Figure 10A:
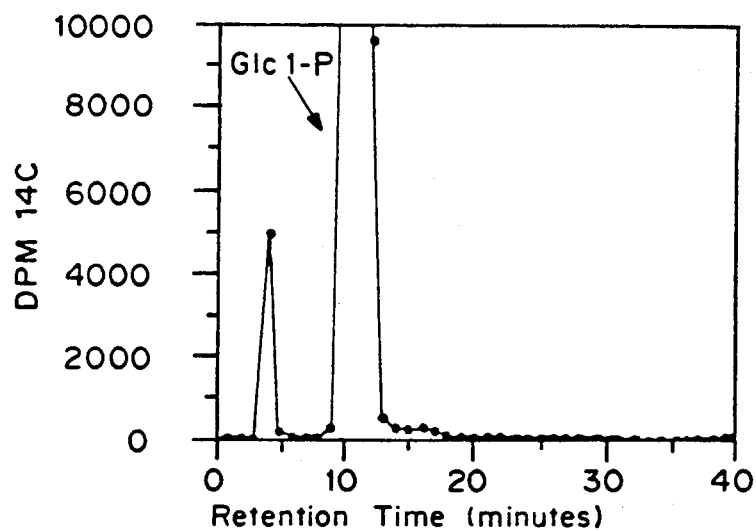
FIG. 10 is a HPLC of [$^{14}C$]-DP-Glc derivatives formed in vitro by incubation of D-[1-$^{14}$ C]Glc 1-P (2.5 mM, 2.8 mCi/mmole) for 4 hours at room temperature in the presence of inorganic pyrophosphatase (2 U), 0.1 mM AzdU-TP and either heat-inactivated UDP-Glc pyrophosphorylase (A) or active UDP-Glc pyrophosphorylase (B). Incubation of UDP-Glc pyrophosphorylase with UTP (C) was performed with similar conditions. Acid-soluble fractions were analyzed by HPLC system A.
Figure 10B:
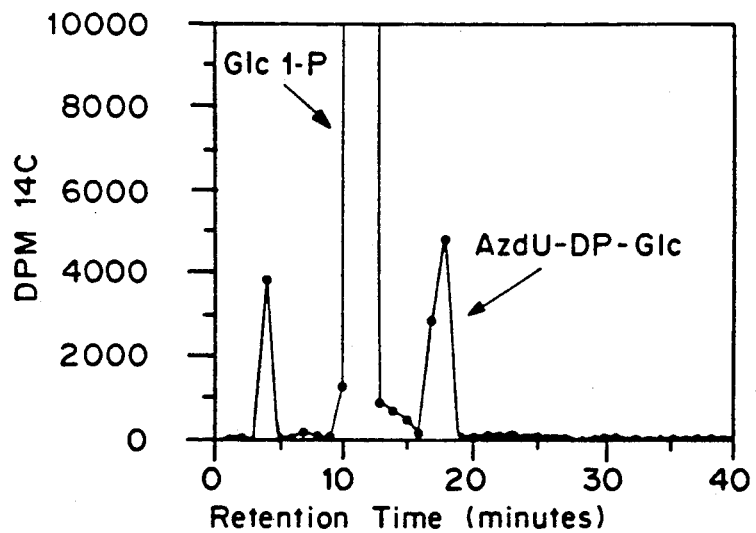
Figure 10C:
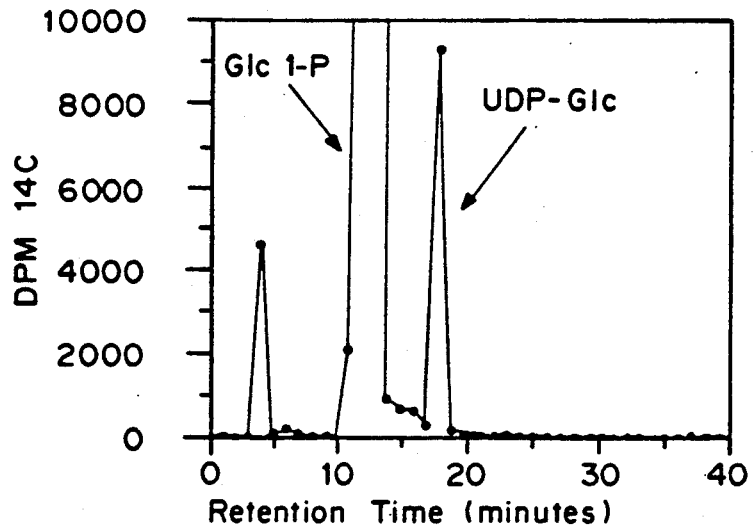

The in vitro formation of the AzdU metabolites was then assessed using pure UDP-Glc pyrophosphorylase in order to elucidate the cellular synthetic pathway of AzdU-DP-hexoses. This enzyme was incubated with 2.5 mM D-[1-$^{14}$C]Glc 1-P (2.8 mCi/mmole) in the presence of chemically synthesized AzdU-TP (0.1 mM). Inorganic pyrophosphatase (2U) was added in the reaction mixture in order to cleave the pyrophosphate formed and keep the reaction unidirectional. The only enzymatically synthesized radiolabeled product formed under these conditions co-eluted with AzdU-$X_2$ detected "in vivo" on the HPLC/carbohydrate system as shown in FIG. 7. In the presence of heat-inactivated enzyme, no radioactivity was found in the AzdU-$X_2$ region and all radioactivity eluted at the same retention time as an authentic Glc 1-P standard (FIG. 10A). Under similar conditions, a positive control experiment was performed using D-[1-$^{14}$C]Glc 1-P and UIP. The radiolabeled product formed had the same retention time as a nonradiolabled UDP-Glc standard (FIG. 10C).

These data suggest that AzdU-$X_2$ represents AzdU-DP-Glc and that this metabolite is formed within cells from AzdU-TP and Glc 1-P by UDP-Glc pyrophosphorylase.

Final identification of the two AzdU sugar nucleotides was obtained by comparing the HPLC retention times of the metabolites in cell extracts and chemically synthesized AzdU metabolites. Using the HPLC/carbohydrate system (system B), the chemically synthesized AzdU-DP-GlcNAc and AzdU-DP-Glc also had retention times of 23 and 26 mins., respectively, thus comigrating with AzdU-$X_1$ and AzdU-$X_2$ detected within cells. In addition, by using HPLC system A, AzdU-DP-GlcNAc and AzdU-DP-Glc eluted together with a retention time of 18 min., similar to that observed initially for "AzdU-X".

It is found that these two AzdU metabolites contribute as much as 20 to 30% of all the AzdU metabolites in both human BMC and PBMC. In contrast, a minimal (less than 3 to 5%) amount of these AzdU-sugar derivatives are detected in U937 and CEM-established cell lines. Since these novel AzdU metabolites are probably derived from AzdU-TP, Glc 1-P, and GlcNAc 1-P catalyzed by UDP-Glc-pyrophosphorylase and UDP-GlcNAc pyrophosphorylase, the relatively small amount of AzdU-sugars in established cell lines, compared to human primary cells, indicates a decreased level of enzymatic activity of the pyrophosphorylases especially since AzdU-TP levels in U937 and CEM cell lines are similar to those found in human PBMC and BMC. A relatively high level of AzdU-DP-hexoses in PBMC and BMC may be explained in part by the conversion of AzdU-TP into those hexose derivatives when there is a sufficient intracellular AzdU supply. This also explains the low AzdU-TP concentrations found in PBMC and undetectable levels in BMC, since the formation of AzdU-DP-Glc and AzdU-DP-GlcNAc by pyrophosphorylases is a reversible reaction, a lack of intracellular AzdU would drive this reaction in reverse, leading to the formation of AzdU-TP from AzdU-DP-hexoses (see, e.g., FIG. 11). In addition, AzdU-DP-Glc and AzdU-DP-GlcNAc may gradually be converted to AzdU-MP by 5'-phosphodiesterase hydrolysis or AzdU-DP by action of glycogen synthase (EC 2.4.1.11), which subsequently is converted to AzdU-TP. This conclusion is consistent with data obtained from metabolite decay experiments and suggests that AzdU is not the only precursor of its 5'-phosphate derivatives within cells. After removal of AzdU from the medium, AzdU-MP and AzdU-DP have long intracellular elimination half-lives, which may reflect conversion of AzdU-DP-hexoses to these 5'-phosphorylated derivatives. In contrast, after removal of AZT from the medium AZT-MP and AZT-DP do no exhibit long intracellular half-lives (Furman, P. A., et al. (1986) supra.). The long elimination half-line of greater than 24 hr of these AzdU-DP-hexoses probably reflects the poor efflux of these compounds.

HPLC Analysis of Intracellular Metabolism of [$^3$H]dUrd in Human PBMC and BMC

Metabolism of dUrd in human primary cells was examined to evaluate whether the previously unrecognized metabolic pathway for AzdU in these cells may be unique to this drug or common the dUrd analogs in general.

Phytohemagglutinin-stimulated PBMC were incubated for 24 hr with 2 $\mu$M [$^3$H]dUrd /S.A. 450 mCi/mmole). Analysis of cell extracts using HPLC system A revealed that the unchanged compound was phosphorylated to its mono-, di- and triphosphate derivatives as expected. An additional chromatographic peak (similar to AzdU) was also observed at 18 minutes.

Concentrations were calculated as the mean ±the standard deviation of at least 3 experiments that were performed with lymphocytes from different donors. The predominant metabolite was dUrd-MP with a concentration of 0.11 ±0.01 pmole/$10^6$ cells, while dUrd-MP and dUrd-TP achieved concentrations of 0.05 ±0.006 and 0.06 ±0.002 pmole/$10^6$ cells, respectively. A concentrations of 0.076±0.01 pmole/$10^6$ cells was calculated for the chromatographic peak detected at 18 min. Similar qualitative and quantitative results were obtained in human BMC.

The chromatographic peak that eluted at 18 min. was resistant to alkaline phosphatase, but was a substrate for venom phosphodiesterase, yielding a single peak of $^3$H-labeled dUrd-MP. Incubation of phytohemagglutin-stimulated PBMC with 2 μM [$^3$H]dUrd (specific activity 300 mCi/mmole) and D-[1-$^{14}$C]Glc (2.2 μCi/ml) led to a doubly-labeled dUrd sugar nucleotide, as ascertained by HPLC analysis of cell extracts. These data demonstrate that not only Urd and/or Urd analogs can be converted to sugar nucleotides but that endogenous dUrd and their analogs may also follow these metabolic pathways with formation of dUrd-DP-hexose derivatives.

E. Cellular Metabolism and Stability of 5'-Diphosphohexose Nucleosides

EXAMPLE 8

Cellular Metabolism of AzdU-DP-gluose in PBM cells and stability of 5'-Diphosphohexose Nucleosides.

Cellular Metabolism

Excess medium was removed from flasks containing 2 day PHA-stimulated human PBM cells, and the number of cells was then determined using a coulter counter. RPMI 1640 medium containing 1% Nutridoma SP (Boehringer Mannheim Biochemials), antibiotics and IL-2 was added to the cells to wash any residual medium, and the cells were harvested.

The Nutridoma medium was then added to dilute the cells to a concentration of $2 \times 10^6$ cells/ml. The cells and medium were transferred into a culture flask. Both cold and radio-labeled AzdU-DP-glucose were added to the flask to give a final concentration of 2 μM (2,000 dpm/pmole). At the selected time, the cells were dispersed, and then 5 ml was removed from the flask, and centrifuged. The pelleted cells were washed once with PBS and centrifuged again (1,000 rpm, 5 minutes, 5° C.). The cells were then transferred to a microcentrifuge tube and extracted overnight with 100 μl 60% methanol:H$_2$O. The cells were extracted two more times (30 minutes each) the next morning. The extracts were combined, lyophilized, and rehydrated with deionized H$_2$O. The solution was then filtered and analyzed on HPLC using a Partisil 10 SAX column, using 10 minutes of 15 mM KH$_2$PO$_4$ pH-3.5 followed with a 45 minute linear gradient to 1M KH$_2$PO$_4$ pH-3.5, with a flow rate of 1 ml min$^{-1}$.

The results of these experiments, which are summarized in Table 2, indicate that substantial amounts of AzdU-DP-glucose are transported intracellularly. This uptake appears to be time dependent, since significantly more radioactivity is found inside the cell after 24 hour treatment.

Stability

High specific activity AzdU-DP-glucose (5 mCi) was synthesized by condensing 5-$^3$H] AzdU-MP with glucose-1-phosphate. The product was highly pure and contained less than 1% AzdU and AzdU-DP.

The stability of the radiolabeled AzdU-DP-glucose was determined at 37° C. in medium containing serum or serum substitute. It was found that AzdU-DP degraded rapidly in serum-containing medium, with close to 50% breakdown to AzdU-MP in about 5 minutes.

The stability of AzdU-DP-glucose was also examined in medium that contained a serum substitute called CPSR-5 (containing bovine embryonic fluid in addition to processed plasma). AzdU-DP-glucose was partially stable in this serum when it was heat inactivated prior to use (see Table 3). Finally, AzdU-DP-glucose was found to be markedly more stable (for at least 24 hours), when the serum-substitute Nutridoma SP is used. Nutridoma SP is commercially available and is composed of chemically defined supplements (including phosphodiesterases) that can completely replace serum and is commonly used for the preparation of hybridoma cell lines. It was added to the medium at the manufacturer recommended concentration (1%).

TABLE 2

Intracellular disposition of [$^3$H] AzdU-DP-glucose (2 μM; 2,000 dpm/pmole) in human cells after exposure for indicated time in medium containing IL-2, antibiotics and 1% NutridomaSP. Nucleoside and nucleotide levels were determined by HPLC.

| Cell Type | AzdU | AzdU-MP | AzdU-DP-glu | AzdU-DP | AzdU-TP |
|---|---|---|---|---|---|
| PBM %$^{a,b}$ | 8.4 | 63.4 | 8.8 | 3.1 | 2.7 |
| pmol/10$^6$ cells | 0.034 | 0.26 | 0.036 | 0.013 | 0.011 |
| dpm/100 μl | 273 | 2.063 | 285 | 100 | 89 |
| PBM cells %$^c$ | 12.0 | 80 | 5.1 | 2.0 | 0.7 |
| pmol/10$^6$ cells | 0.95 | 6.30 | 0.41 | 0.16 | 0.031 |
| dpm | 7.564 | 50.259 | 3.238 | 1.243 | 247 |

$^a$Percent of total intracellular radioactivity.
$^b$Time of uptake, one hour.
$^c$Time of uptake, 24 hours.

TABLE 3

Stability of [5-$^3$H] AzdU-DP-glucose in RPMI 1640 medium containing different serum or serum substituted at 37° C. Media also contained antibiotics and interleukin-2. Nucleoside and nucleotide analysis was performed by HPLC.

| Medium with | Time % AzdU | % AzdU-MP | % AzdU-DP-glu |
|---|---|---|---|
| FCS (20%)$^a$ | 0 minutes | 0 | 0 | 100 |
| | 5 minutes | 1.1 | 48.9 | 49.7 |
| | 10 minutes | 1.9 | 69.8 | 28.1 |
| | 20 minutes | 3.6 | 82.7 | 13.2 |
| | 40 minutes | 7.3 | 88.7 | 3.5 |
| | 60 minutes | 11.4 | 86.3 | 1.6 |
| CPSR-5 (20%)$^b$ | 1 hour | 0.7 | 17.4 | 80.8 |
| | 6 hours* | 0.7 | 44.8 | 53.8 |
| | 24 hours* | 2.2 | 59.7 | 6.7 |
| Nutridoma SP (1%)$^c$ | 1 hour | 0 | 5.1 | 94.2 |
| | 24 hours | 0 | 8.8 | 90.5 |

$^a$Gibco;
$^b$Sigma (heat inactivated for 60' at 56° C.);
$^c$Boehringer Mannheim Biochemicals;
*PBM cells present

Preparation of 5'-Diphosphohexose Nucleoside Pharmaceutical Compositions

In the preferred embodiment for therapeutic use, the compounds are provided in a pharmaceutical carrier in an amount sufficient to exhibit the desired biological activity in vivo, or the desired in vitro activity in any biological solution containing cells. 5'-Diphosphohexose nucleosides can be used for both in vitro and in vivo therapeutic use to increase absorption and or activity of biologically active nucleosides. Alternatively, as described in detail above, many of the 5'-diphosphohexose nucleosides have unique biological activity. For example, the composition can be used for inhibition of HIV in cell cultures, and in the production of pharmaceutical products. The composition is also of value in blood banking procedures.

Pharmaceutical carriers suitable for administration of the compounds are known to those skilled in the art, depending on the mode of administration. The active materials can be administered by any appropriate route, for example, orally, parenterally, intravenously, intradermally, subcutaneously, or topically, in liquid or solid form. Because of the enhanced biological activity, the effective dosage of the derivatized nucleosides may be less than the effective dosage of the underivatized nucleoside. For example, the effective dosage of 3'-azido-2',3'-dideoxyuridine-5'-diphosphohexose to treat HIV is approximately ten times lower than the effective dosage of the parent compound, 3'-azido-2', 3'-dideoxyuridine.

The active compound is included in the pharmaceutically acceptable carrier in an amount sufficient to exert a therapeutically useful effect in the absence of serious toxic effects on the patient treated. For example, an "HIV inhibitory amount" is an amount of active ingredient sufficient to exert an HIV inhibitory effect as measured by an assay such as the one described in Example 2. These preparations should produce a serum concentration of active ingredient of from about 0.2 to 40 $\mu$M. A preferred concentration range is from 0.2 to 20 $\mu$M and most preferably about 1 to 10 $\mu$M. The pharmaceutical compositions should provide a dosage of from 1 to 60 milligrams of compound per kilogram of body weight per day.

The concentration of active compound in the drug composition will depend on absorption, inactivation, and excretion rates of the active compound as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions. The active ingredient may be administered at once, or may be divided into a number of smaller doses to be administered at varying intervals of time.

5'-Diphosphohexose nucleosides are dephosphorylated in the presence of certain enzymes, in particular phosphodiesterases. Therefore, the compounds must be administered in a way that protects them until they can reach the target organism. A preferred means of protecting the compounds is by administering them in a liposomal suspension, either intraperitoneally, subcutaneously, or intravenously. Liposomes can also be administered orally but must be protected during uptake by the bloodstream to avoid degradation and exposure of the encapsulated drug to phosphodiesterases while in the gastrointestinal tract. A wide variety of liposomes are known to those in the art, including liposomes targeted to infected cells (such as macrophage cells). These can be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the diphosphohexose nucleoside derivative is then introduced into the container, the container is swirled by hand to free lipid material from the sides of the container and to disperse lipid aggregates, and thereby form the liposomal suspension.

Other compositions known to those skilled in the art can also be used for drug delivery, especially oral delivery. For example, protein microspheres of less than five microns in diameter can be absorbed intact through the gastrointestinal tract into the blood stream, where they are phagocytized by the macrophages or degrade to release the drug. Drug is dispersed into the protein solution prior to forming the microsphere to incorporate the drug into the microsphere. Methods for making these microspheres are known to those skilled in the art, for example, as described in U.S. Pat. No. 4,925,673 to Steiner, et al.

EXAMPLE 8

Incorporation of Liposomes containing 5'-Diphosphohexose Nucleoside into Human PBM cells To human PBM cells ($4.2 \times 10^6$ cells/ml) in a final volume of 15 ml of growth medium containing serum substitute, was added AzdU-DP-glucose containing liposomes (1.8 ml of 1.47 mM). The mix was incubated at 37° C. for 1 hour, and was gently mixed every 5 minutes. After 1 hour the cells were harvested by centrifugation (5 min, 1000 rpm). The cells were washed once with cold phosphate buffered saline and recentrifuged. To the cell pellet was added methanol:$H_2O$ (60%; 200 $\mu$l). The suspension was extracted overnight, centrifuged (1 min, 13,000 rpm), and the supernatent removed. The pellet was extracted twice more for 30 minutes each. The extracts were pooled, lyopholyzed, resuspended (250 $\mu$l), filtered and analyzed on HPLC. HPLC analysis was initiated with 10 minutes of 15 mM $KH_2PO_4$ pH 3.5 followed by a linear gradient of 45 minutes to 1M $KH_2PO_4$ pH 3.5. The flow rate was 1 ml/min. One ml fractions were collected, and counted on a scintillation counter. The HPLC is illustrated in FIG. 12.

Figure 12:
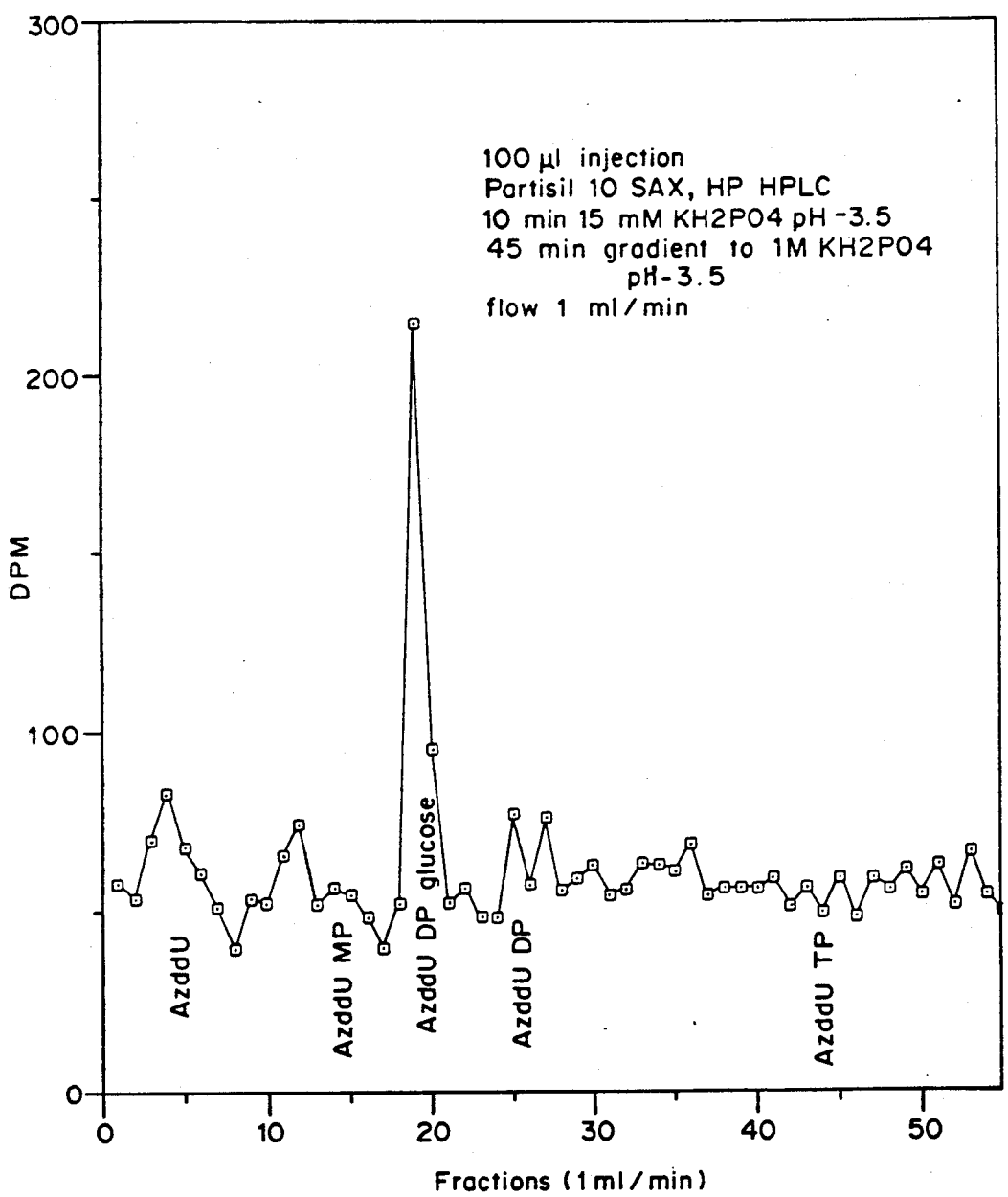
FIG. 12 is the HPL chromatogram of the extract of PBM cells incubated one hour with liposomes containing AzddU-DP-glucose. 100 μl of cell extract was injected into a Partisil 10 SAX. HP HPLC column eluted 10 min with 15 mM KH₂PO₄, pH 3.5, followed by a 45 min gradient to 1M KH₂PO₄, pH 3.5, at 1 ml/min.

As shown in FIG. 12, the HPLC profile of the cell extract indicated that the liposome containing drug is incorporated into the cells after incubation for one hour. A single peak for the drug corresponding to unchanged AzddU-DP-glucose was found. This experiment suggests that liposomes containing drug can be used to deliver drug to human lymphocytes.

Some compounds, such as 2',3'-dideoxyadenosine and 2',3'-dideoxy-$N^6$-methyladenosine, and their 5'-diphosphohexose derivatives that have anti-HIV activity, are acid labile. If oral administration is desired, the compound must be provided in a composition that protects it from the acidic environment of the stomach. The compound can be orally administered in combination with an antacid formulation. The composition can also be administered in an enteric coating that maintains its integrity in the stomach and releases the active compound in the intestine.

A preferred mode of administration of the compounds of this invention is oral. Oral compositions will generally include an inert diluent or an edible carrier. The composition can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid. Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antibiotics, antifungals, antiinflammatories, or other antivirals, including those without 5'-diphosphohexose groups, or anticancer compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceutical, Inc.

Modifications and variations of the 5-diphosphohexose compounds, pharmaceutical preparations and methods of use thereof, will be apparent to those of skill in the relevant art from the foregoing detailed description. Such modifications and variations are intended to come with the scope of the following claims.

We claim:

1. A pharmaceutical composition comprising a compound of the formula

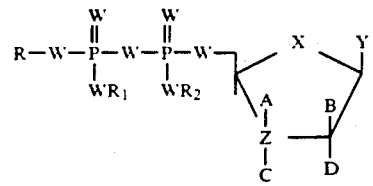

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; $R_1$ and $R_2$ are hydrogen or alkyl groups from $C_1$ to $C_{10}$, W is oxygen or sulfur; X is oxygen, sulfur or $CH_2$; Y is a purine or pyrimidine base, and Z is carbon, sulfur, or oxygen, and wherein when Z is sulfur or oxygen, A and C are not present, or its pharmaceutically acceptable salt, and a pharmaceutical carrier.

2. The composition of claim 1 in a dose effective for the treatment of a microbial infection.

3. The composition of claim 2, wherein the microbial infection is an opportunistic infection.

4. The composition of claim 3, wherein the opportunistic infection is caused by a microorganism selected from the group consisting of *M. avian intracellulare, M. tuberculosis*, Legionella sp., *Pneumocystis carinii* pneumoniae, Salmonella sp., Shigella sp., toxoplasmosis, chronic cryptococcosis, histoplasmosis, cytomegalovirus, and a member of the genus Mycoplasma.

5. The composition of claim 2 in a dose effective for the treatment of an antiviral infection.

6. The composition of claim 2 in a dose effective for the treatment of an HIV infection.

7. The composition of claim 2 in a dose effective for the treatment of a bacterial infection.

8. The composition of claim 1, wherein the pharmaceutically acceptable carrier includes a liposome.

9. The composition of claim 1, further comprising an active agent selected from the group consisting of antibiotics, antifungals, antiinflammatories, nucleosides without 5'-diphosphohexose groups, antiviral compounds, and anticancer compounds.

* * * * *